(12) United States Patent
Veerabhadrappa et al.

(10) Patent No.: US 10,106,482 B2
(45) Date of Patent: *Oct. 23, 2018

(54) SYNTHESIS OF MAGNESIUM ADAMANTANE SALTS AND MAGNESIUM OXIDE NANOCOMPOSITES, AND SYSTEMS AND METHODS INCLUDING THE SALTS OR THE NANOCOMPOSITES

(71) Applicants: Saudi Arabian Oil Company, Dhahran (SA); Durham University, Durham (GB)

(72) Inventors: Manohara Gudiyor Veerabhadrappa, Durham (GB); Hugh Christopher Greenwell, Durham (GB); Gasan Selman Alabedi, Cheshire (GB); John Adrian Hall, Dhahran (SA); Andrew Whiting, Durham (GB)

(73) Assignees: Saudi Arabian Oil Company, Dhahran (SA); Durham University, Durham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/453,180

(22) Filed: Mar. 8, 2017

(65) Prior Publication Data
US 2017/0267620 A1  Sep. 21, 2017

Related U.S. Application Data

(60) Provisional application No. 62/309,657, filed on Mar. 17, 2016.

(51) Int. Cl.
*C07C 57/12* (2006.01)
*B01J 21/18* (2006.01)
(Continued)

(52) U.S. Cl.
CPC ......... *C07C 51/418* (2013.01); *B01J 31/0205* (2013.01); *B01J 37/04* (2013.01);
(Continued)

(58) Field of Classification Search
CPC ........ B01J 21/18; B01J 23/02; B01J 35/0006; B01J 37/04; B01J 37/086; B01J 2523/22;
(Continued)

(56) References Cited

U.S. PATENT DOCUMENTS 3,342,880 A * 9/1967 Reinhardt ............... C07C 17/10
526/282
3,671,432 A   6/1972 Peters et al.
(Continued)

FOREIGN PATENT DOCUMENTS

CA   2594060 A1   6/2006
CN  105017485 A  11/2015
(Continued)

OTHER PUBLICATIONS

Jagadese J. Vidal, "The Chemistry of Inorganic and Organometallic Compounds with Adamantane-Like Structures." Polyhedron, vol. 15, No. 10 (1996), pp. 1585-1642.*
(Continued)

*Primary Examiner* — Patricia L. Hailey
(74) *Attorney, Agent, or Firm* — Dinsmore & Shohl LLP

(57) ABSTRACT

A method for preparing a magnesium adamantane carboxylate salt is provided. The method includes mixing a magnesium salt and a diamondoid compound having at least one carboxylic acid moiety to form a reactant mixture and hydrothermally treating the reactant mixture at a reaction temperature for a reaction time to form the magnesium adamantane carboxylate salt.

17 Claims, 13 Drawing Sheets

(51) Int. Cl.

| | |
|---|---|
| *B01J 23/02* | (2006.01) |
| *C07C 51/41* | (2006.01) |
| *B01J 31/02* | (2006.01) |
| *B01J 37/04* | (2006.01) |
| *B01J 37/08* | (2006.01) |
| *B01J 37/10* | (2006.01) |
| *C01F 5/00* | (2006.01) |

(52) U.S. Cl.
CPC .............. *B01J 37/082* (2013.01); *B01J 37/10* (2013.01); *C01F 5/00* (2013.01); *C01P 2002/72* (2013.01); *C01P 2002/82* (2013.01); *C01P 2004/03* (2013.01); *C01P 2004/04* (2013.01); *C07C 2103/88* (2013.01)

(58) Field of Classification Search
CPC ................ B01J 2531/22; C07C 51/412; C07C 2523/02; C07C 2603/74
USPC ................... 502/170, 183; 585/352; 568/818
See application file for complete search history.

(56) References Cited

U.S. PATENT DOCUMENTS

| | | | |
|---|---|---|---|
| 4,021,371 A | | 5/1977 | Petro et al. |
| 4,419,222 A | | 12/1983 | Grenoble et al. |
| 4,774,212 A | | 9/1988 | Drezdon |
| 4,952,748 A | | 8/1990 | Alexander et al. |
| 4,956,481 A | * | 9/1990 | Gillaspey ............. A24B 15/345 510/104 |
| 5,021,184 A | * | 6/1991 | Gillaspey ............. A24B 15/345 131/277 |
| 5,073,532 A | | 12/1991 | Domesle et al. |
| 5,260,495 A | | 11/1993 | Forkner |
| 5,326,891 A | | 7/1994 | Breuer et al. |
| 5,399,329 A | | 3/1995 | Schutz et al. |
| 5,635,457 A | | 6/1997 | Van Slyke |
| 5,883,041 A | | 3/1999 | Pak et al. |
| 6,096,690 A | | 8/2000 | Wittenbrink et al. |
| 6,323,270 B1 | | 11/2001 | Ishida |
| 6,410,635 B1 | | 6/2002 | Kaylo et al. |
| 6,429,314 B1 | * | 8/2002 | Ishii ........................ C07B 41/06 546/112 |
| 7,098,366 B2 | | 8/2006 | Sigl et al. |
| 7,129,287 B1 | | 10/2006 | Lee et al. |
| 7,557,063 B2 | | 7/2009 | Hagemeyer et al. |
| 7,582,202 B2 | | 9/2009 | Jones et al. |
| 7,918,935 B2 | | 4/2011 | Park et al. |
| 8,034,867 B2 | | 10/2011 | Abarca et al. |
| 8,088,349 B2 | | 1/2012 | Duan et al. |
| 8,158,843 B2 | | 4/2012 | Song et al. |
| 8,613,900 B2 | | 12/2013 | Frei et al. |
| 8,652,994 B2 | | 2/2014 | Li et al. |
| 2002/0110520 A1 | | 8/2002 | Stamires et al. |
| 2008/0108498 A1 | | 5/2008 | Duan et al. |
| 2008/0207801 A1 | | 8/2008 | Ton-That et al. |
| 2010/0279848 A1 | | 11/2010 | Iyi et al. |
| 2011/0237430 A1 | | 9/2011 | Zhang et al. |
| 2011/0248314 A1 | * | 10/2011 | Takei ........................ C08L 83/04 257/100 |
| 2012/0058739 A1 | | 3/2012 | McKinzie, III et al. |
| 2012/0258857 A1 | | 10/2012 | Pham et al. |
| 2012/0312344 A1 | | 12/2012 | Delorme |
| 2012/0322694 A1 | | 12/2012 | Monteiro et al. |
| 2013/0116351 A1 | | 5/2013 | Querner et al. |
| 2013/0143731 A1 | | 6/2013 | Li et al. |
| 2013/0172642 A1 | | 7/2013 | Behrens et al. |
| 2013/0260990 A1 | | 10/2013 | Kwon et al. |
| 2014/0113196 A1 | | 4/2014 | Balaya et al. |
| 2015/0027710 A1 | | 1/2015 | Miller |
| 2017/0029375 A1 | * | 2/2017 | Harichian ............. C07D 215/08 |
| 2017/0266642 A1 | * | 9/2017 | Veerabhadrappa ........................ B01D 53/8671 |
| 2017/0267620 A1 | * | 9/2017 | Veerabhadrappa ........................ B01J 31/0205 |
| 2017/0267623 A1 | * | 9/2017 | Veerabhadrappa ... C07C 61/135 |
| 2017/0267910 A1 | * | 9/2017 | Mohammed ............ C07C 51/60 |

FOREIGN PATENT DOCUMENTS

| | | |
|---|---|---|
| EP | 1419817 A1 | 5/2004 |
| EP | 1952885 A1 | 8/2008 |
| EP | 2263976 A1 | 12/2010 |
| WO | 0224756 A2 | 3/2002 |
| WO | 2013007993 A2 | 1/2013 |
| WO | 2013072197 A1 | 5/2013 |
| WO | 2014037378 A1 | 3/2014 |
| WO | 2014052510 A1 | 4/2014 |
| WO | 2014080428 A1 | 5/2014 |

OTHER PUBLICATIONS

Cavani et al., Hydrotalcite-Type Anionic Clays: Preparation, Properties and Applications, Catalysis Today, vol. 11, 1991, 173-301, Elsevier Science Publishers B.V.

Chang, et al., "Ca-Rich Ca—Al-Oxide, High-Temperature-Stable Sorbents Prepared from Hydrotalcite Precursors: Synthesis, Characterization, and CO2 Capture Capacity", ChemSusChem, 2011, vol. 4, 1844-1851, Wiley-VCH.

Chen, et al., "Preparation and Characterization of Flexible Asymmetric Supercapacitors Based on Transition-Metal-Oxide Nanowire/Single-Walled Carbon Nanotube Hybrid Thin-Film Electrodes", ACSNano, 2010, vol. 4, No. 8, 4403-4411, American Chemical Society.

Damodara et al., "Copper Nanoparticles from Copper Aluminum Hydrotalcite: An Efficient Catalyst for Acceptor- and Oxidant-Free Dehydrogenation of Amines and Alcohols", Adv. Synth. Catal., 2014, vol. 356, 189-198, Wiley-VCH.

Del Arco et al., "Release studies of different NSAIDS encapsulated in Mg, Al, Fe-hydrotalcites" Applied Clay Science, vol. 42, 2009, 538-544, Elsevier B.V.

Ding, et al., "Equilibria and kinetics of CO2 absorption on hydrotalcite adsorbent" Chemical Engineering Science, 2000, vol. 55, 3461-3474, Elsevier Science Ltd.

Gardolinski et al., "Grafted organic derivatives of kaolinite: II. Intercalation of primary n-alkylamines and delamination", Clay Minerals, 2005, vol. 40, 547-556, The Mineralogical Society.

Itoh, et al., Nanoscale Metal Oxide Particles as Chemical Reagents. Intrinsic Effects of Particle Size on Hydroxyl Content and on Reactivity and Acid/Base Properties of Ultrafine Magnesium Oxide, Chem. Mater. 1993, vol. 5, 71-77, American Chemical Society.

Khan, et al., "Intercalation chemistry of layered double hydroxides: recent developments and applications", Journal of Materials Chemistry, 2002, vol. 12, 3191-3198, The Royal Society of Chemistry.

Kumar, et al., "Sonochemical Synthesis and Characterization of Nanometer-Size Transition Metal Oxides from Metal Acetates" Chem. Mater. 2000, vol. 12, 2301-2405, American Chemical Society.

Kumbhar, et al., Reduction of Aromatic Nitro Compounds with Hydrazine Hydrate in the Presence of the Iron(III) Oxide-MgO Catalyst Prepared from a Mg—Fe Hydrotalcite Prescursor, Tetrahedron Letters, 1998, vol. 39, 2573-2574, Elsevier Science Ltd.

Kumbhar, et al., Mg—Fe Hydrotalcite as a Catalyst for the Reduction of Aromatic Nitro Compounds with Hydrazine Hydrate, Journal of Catalysis, 2000, vol. 191, 467-473, Academic Press.

Li et al., "Mg(OH)2@reduced graphene oxide composite for removal of dyes from water", Journal of Materials Chemistry, 2011, vol. 21, 13765-13768, The Royal Society of Chemistry.

Meyn et al., "Anion-Exchange Reactions of Layered Double Hydroxides"Inorg. Chem. 1990, vol. 29, 5201-5207, American Chemical Society.

Miyata, Shigeo, "Physico-Chemical Properties of Synthetic Hydrotalcites in Relation to Composition", Clays and Clay Minerals, 1980, vol. 28, No. 1, 50-56, The Clay Minerals Society.

(56) References Cited

OTHER PUBLICATIONS

Mulukutla, C. Detellier, "Thermally activated Mg, Fe layered double hydroxide as reductant for nitric oxide", Journal of Materials Science Letters 1996, vol. 15, 797-799, Chapman & Hall.

Nethrvathi, et al., Cobalt Hydroxide/Oxide Hexagonal Ring-Graphene Hybrids through Chemical Etching of Metal Hydroxide Platelets by Graphene Oxide: Energy Storage Applications, ASCNano, 2014, vol. 8, No. 3, 2755-2765, American Chemical Society.

Poizot et al., Nano-sized transition-metal oxides as negative-electrode materials for lithium-ion batteries, Nature, 2000, vol. 407, pp. 496-499, Macmillan Magazines Ltd.

Prasanna, et al., Chromate uptake characteristics of pristine layered double hydroxides of Mg with Al, Solid State Sciences, 2008, vol. 10, 260-266, Elsevier Masson SAS.

Reichle, Walter T., "Catalytic Reactions by Thermally Activated Anionic Clay Minerals" Journal of Catalysis, 1985, vol. 94, 547-557, Academic Press, Inc.

Shukla, et al., "Stabilized a-Ni(OH)2 as Electrode Material for Alkaline Secondary Cells", J. Electrochem Soc., 1994, vol. 141, No. 11, 2956-2959, The Electrochemical Society, Inc.

Tao et al., "A redox-stable efficient anode for solid-oxide fuel cells" Nature Materials, 2003, vol. 2, 320-323, Nature Jublishing Group.

Wang, et al., "Synthesis of high-temperature CO2 adsorbents from organo-layered double hydroxides with markedly Improved CO2 capture capacity" The Royal Society of Chemistry, 2012, vol. 5, 7526-7530, Energy Environ. Sci.

White et al., Supported metal nanoparticles on porous materials. Methods and Applications; The Royal Society of chemistry 2009, vol. 38, 481-494, Chemical Society Reviews.

Williams, et al., "Towards understanding, control and application of layered double hydroxide chemistry", Journal of Materials Chemistry, 2006, vol. 16, 3065-3074, Journal of Materials Chemistry.

Yao, et al., "Confined adamantane molecules assembled to one dimension in carbon nanontubes" Carbon, 2011, vol. 49, 1159-1166, Elsevier Ltd.

Yavuz, et al., "Markedly Improved CO2 Capture Efficiency and Stability of Gallium Substituted Hydrotalcites at Elevated Temperatures" Chem. Mater. 2009, vol. 21, 3473-3475, American Chemical Society.

Zhao et al., "Carbon Nanowire Made of a Long Lineal Carbon Chain Inserted Inside a Multiwalled Carbon Nanotube", Physical Review Letters, 2003, vol. 90, No. 18, 187401-1-187401-4, The American Physical Society.

International Search Report dated Jul. 13, 2017, pertaining to PCT/US2017/021550, filed Mar. 9, 2017, 8 pages.

Written Opinion dated Jul. 13, 2017, pertaining to PCT/US2017/021550, filed Mar. 9, 2017, 13 pages.

J. Costantino, et al., Preparation and characterization of hydrotalcite/carboxyadamantane intercalation compounds as fillers of polymeric nanocomposites, Journal of Materials Chemistry, vol. 17, No. 11, Dec. 22, 2006, pp. 1079-1086.

Goh, et al., Application of layered double hydroxides for removal of oxyanions: A review, Water Research, Elsevier, vol. 42, No. 6-7, Nov. 7, 2007, pp. 1343-1368, Amsterdam, Netherlands.

Kanezaki, Unexchangeable Interlayer Anions: Synthesis and Characterization of Zn/Al- and Mg/Al-Layered Double Hydroxides with Interlayer Alizarin red S, Journal of Inclusion Phenomena and Macrocyclic Chemistry, Jun. 1, 2003, pp. 89-95, https://rd.springer.com.

Crepaldi, et al., Sorption of terephthalate anions by calcined and uncalcined hydrotalcite-like compounds, Colloids and Surfaces A: Physicochem. Eng. Aspects 211, vol. 211, No. 2-3, Jun. 4, 2002, pp. 103-114, Amsterdam, Netherlands.

Sabbar, et al., Probing the interaction between di- and tri-functionalized carboxy-phosphonic acid and LDH layer structure, Journal of Physics and Chemistry of Solids, Pergamon Press, vol. 67, No. 11, Sep. 6, 2006, pp. 2419-2429, London, England.

Lima, et al., Characterization of basic catalysts by the use of nitromethane as NMR probe molecule and reactant, Journal of Cataly, Academic Press, vol. 223, No. 1, Feb. 20, 2004, pp. 28-35, USA.

Khan, et al., The intercalation of bicyclic and tricyclic carboxylates into layered double hydroxides, Journal of Solid State Chemistry, vol. 183, No. 12, Sep. 30, 2010, pp. 2877-2885, USA.

Moorhead-Rosenberg et al., "A Rapid Microwave-Assisted Solvothermal Approach to Lower-Valent Transition Metal Oxides", Inorg. Chem., 2013, 52, 13087-13093, American Chemical Society.

Schwertfeger et al., "Diamonds are a Chemist's Best Friend: Diamondoid Chemistry Beyond Adamantane", Angew. Chem. Int. Ed., 2008, 47, 1022-1036, Wiley-VCH GmbH & Co.

Schwertmann et al., "The Formation of Green Rust and Its Transformation to Lepidocrocite", Clay Minerals, 1994, 29, 87-92, The Mineralogical Society.

Singoredjo et al., "Alumina Supported Manganese Oxides for the Low-Temperature Selective Catalytic Reduction of Nitric Oxide with Ammonia", Applied Catalysis B: Environmental, 1992, 1, 297-316, Elsevier Science Publishers B.V.

Spaldin et al., "The Renaissance of Magnetoelectric Multiferroics", Science, 2005, 309, 391-392, AAAS.

Spyrou et al., "Towards Novel Multifunctional Pillared Nanostructures: Effective Intercalation of Adamantylamine in Graphene Oxide and Smectite Clays", Adv. Funct. Mater., 2014, 24, 2841-5850, Wiley-VCH Verlag GmbH & Co.

Stankic et al., "Size-Dependent Optical Properties of MgO Nanocubes", Angew. Chem. Int. Ed., 2005, 44, 4917-4920, Wiley-VCH Verlag GmbH & Co.

Stein et al., "Salt-Gel Synthesis of Porous Transition-Metal Oxides", Chem. Mater., 1995, 7, 304-313, American Chemical Society.

Tao et al., "Synthesis and Characterization of Layered Double Hydroxides with a High Aspect Ratio", Journal of Solid State Chemistry, 2006, 179, 708-715, Elsevier Inc.

Tian et al., "Manganese Oxide Mesoporous Structures: Mixed-Valent Semiconducting Catalysts", Science, 1997, 276, 926-930.

Tokura et al., "Orbital Physics in Transition-Metal Oxides", Science, 2000, 288, 462-468.

Vidal-Michel et al., "Effect of Crystal Size on the Oxidative Dehydrogenation of Butane on V/MgO Catalysts", Journal of Catalysis, 2004, 221, 127-136, Elsevier Inc.

Walia et al., "Transition Metal Oxides—Thermoelectric Properties", Progress in Materials Science, 2013, 58, 1443-1489, Elsevier Ltd.

Wang et al., "Electronics and Optoelectronics of Two-Dimensional Transition Metal Dichalcogenides", Nature Nanotechnology, 2012, 7, 699-712, Macmilan Publishers.

Wang et al., "CO2 Capture by Solid Adsorbents and Their Applications: Current Status and New Trends", Energy Environ. Sci., 2011, 4, 42-55, The Royal Society of Chemistry.

Westerhaus et al., "Heterogenized Cobalt Oxide Catalysts for Nitroarene Reduction by Pyrolysis of Molecularly Defined Complexes", Nature Chemistry, 2013, 5, 537-543.

Xie et al., "Low-Temperature Oxidation of CO Catalysed by Co3O4 Nanorods", Nature, 2009, 458, 746-749, Macmilian Publishers Limited.

Xu et al., "Surface Area and Thermal Stability Effect of the MgO Supported Catalysts for the Synthesis of Carbon Nanotubes", Journal of Materials Chemistry, 2008, 18, 5738-5745, The Royal Society of Chemistry.

Zhang et al., "Synthesis and Transformation of Linear Adamantane Assemblies Inside Carbon Nanotubes", ACS Nano, 6:10, 8674-8683.

Zhang et al., "Hydrogen Production via the Direct Cracking of Methane Over Silica-Supported Nickel Catalysts", Applied Catalysts A: General, 1998, 167, 161-172, Elsevier B.V.

Zhuang et al., "Comparative Study on the use of Cationic-Nonionic-Organo-Montmorillonite in Oil-Based Drilling Fluids", Applied Clay Science, 2015, 116-117, 257-262, Elsevier B.V.

International Search Report and Written Opinion pertaining to PCT/US2017/021135 dated Jun. 12, 2017.

International Search Report and Written Opinion pertaining to PCT/US2017/022427 dated Jun. 12, 2017.

(56) References Cited

OTHER PUBLICATIONS

International Search Report and Written Opinion pertaining to PCT/US2017/021478 dated May 29, 2017.

Lu et al., "Sheet-like and Fusiform CuO Nanostructures Grown on Graphene by Rapid Microwave Heating for High Li-Ion Storage Capacities", J. Mater. Chem., 2011, 21, 17916.

Huang et al., "Controllable Preparation of Nano-MgO and Investigation of its Bactericidal Properties", Journal of Inorganic Biochemistry, 2005, 99, 986-996.

Chen et al., "Cu2(ATC) 6H2O: Design of Open Metal Sites in Porous Metal-Organic Crystals (ATC: 1,3,5,70Adamantane Tetracarboxylate", J. Am. Chem. Soc., 2000, 122, 11559-11560.

Kim et al., "Assembly of Metal-Organic Frameworks from Large Organic and Inorganic Secondary Building Units: New Examples and Simplifying Principles for Complex Structures", J. Am. Chem. Soc., 2001, 123, 8239-8247.

International Search Report dated Jul. 13, 2017, pertaining to PCT/US2017/022485, filed Mar. 15, 2017, 7 pages.

Written Opinion dated Jul. 13, 2017, pertaining to PCT/US2017/022485, filed Mar. 15, 2017, 11 pages.

Abdo et al., "Clay Nanoparticles Modified Drilling Fluids for Drilling of Deep Hydrocarbon Wells", Applied Clay Science, 2013, 86, 76-82, Elsevier B.V.

Abdou et al., "Evaluation of Egyptian Bentonite and Nano-Bentonite as Drilling Mud", Egyptian Journal of Petroleum, 2013, 22, 53-59, Egyptian Petroleum Research Institute.

Alvarado et al., "Preparation and Characterization of MgO Powders Obtained from Different Magnesium Salts and the Mineral Dolomite", Polyhedron, 2000, 19, 2345-2351, Elsevier Science B.V.

Baltes et al., "Synthesis of Supported Transition Metal Oxide Catalysts by the Designed Deposition of Acetylacetonate Complexes", Langmuir, 1999, 15, 5841-5845, American Chemical Society.

Bednorz et al., "Possible HIgh Tc Superconductivity in the Ba—La—Cu—O System", Condensed Matter, 1986, 64, 189-193, Springer-Verlag.

Bernholc et al., "Bronsted Acid Sites in Transition Metal Oxide Catalysts: Modeling of Structure, Acid Strengths, and Support Effects", J. Phys. Chem., 1987, 91, 1526-1530, American Chemical Society.

Cao et al., "Ultra-High Capacity Lithium-Ion Batteries with Hierarchical CoO Nanowire Clusters as Binder Free Electrodes", Advanced Functional Materials, 2015, 25, 1082-1089, Wiley-VCH Verlag GmbH & Co.

Cao et al., "Mg(OH)2 Complex Nanostructures with Superhydrophobicity and Flame Retardant Effects", J. Phys. Chem., 2010, 114, 17362-17368, American Chemical Society.

Choudary et al., "Benzylation of Aromatic Compounds with Different Crystallites of Mgo", Journal of American Chemical Society, 2003, 125, 2020-2021, American Chemical Society.

Di Cosimo et al., "Basic Catalysis on MgO: Generation, Characterization and Catalytic Properties of Active Sites", Catalysis, 2014, 26, 1-28.

Gardolinski et al., "Grafted Organic Derivatives of Kaolinite: I. Synthesis, Chemical and Rheological 2 Characterization", Clay Minerals, 2005, 40, 537-546, The Mineralogical Society.

Guo et al., "A Comprehensive Review on Synthesis Methods for Transition-Metal Oxide Nanostructures", CrystEngComm, 2015, 17, 3551-3585, The Royal Society of Chemistry.

Haber, Jerzy, "Catalysis by Transition Metal Oxides", ACS Symposium Series, Washington D.C., 1985, Grasselli and Brazdil: Solid State Chemistry in Catalysis, American Chemical Society.

Hermoso et al., "Influence of Viscosity Modifier Nature and Concentration on the Viscous Flow Behaviour of Oil-Based Drilling Fluids at High Pressure", Applied Clay Science, 2014, 87, 14-21, Elsevier B.V.

Hsueh et al., "Preparation and Properties of LDHs/Epoxy Nanocomposites", Polymer, 2003, 44, 5275-5283, Elsevier Ltd.

Huang et al., "Removal of NO by Reversible Adsorption on Fe—Mn Based Transition Metal Oxides", Langmuir, 2001, 17, 4997-5003, American Chemical Society.

Jagadeesh et al., "Selective Oxidation of Alcohols to Esters Using Heterogeneous Co3O4—N@C Catalysts Under Mild Conditions", Journal of the American Chemical Society, 2013, 135, 10776-10782, American Chemical Society.

Jiancheng et al., "A New Type of Whole Oil-Based Drilling Fluid", Petrol. Explor. Develop., 2014, 41(4), 538-544, Elsevier B.V.

Johnson, Mark, "Spintronics", J. Phys. Chem. B, 2005, 109, 14278-14291, American Chemical Society.

Kelkar et al., "Mi-, Mg- and Co-Containing Hydrotalcite-Like Materials with a Sheet-Like Morphology: Synthesis and Characterization", Microporous Materials, 1997, 10, 163-172, Elsevier Science BV.

Krishnamoorthy et al., "Catalytic Oxidation of 1,2-Dichlorobenzene Over Supported Transition Metal Oxides", Journal of Catalysis, 2000, 193, 264-272, Academic Press.

Kumar et al., "Sonochmical Synthesis and Characterization of Nanometer-Size Transition Metal Oxides from Metal Acetates", Chem .Mater., 2000, 12, 2301-2305, American Chemical Society.

Kumar et al., "Effect of MgO Nanoparticles on Ionic Conductivity and Electrochemical Properties of Nanocomposite Polymer Electrolyte", Journal of Membrane Science, 2007, 300, 104-110, Elsevier B.V.

Lebaron et al., "Polymer-Layered Silicate Nanocomposites: An Overview", Applied Clay Science, 1999, 15, 11-29, Elsevier Science B.V.

Li et al., "Electroreduction of Carbon Monoxide to Liquid Fuel on Oxide-Derived Nanocrystalline Copper", Nature, 2014, 508, 504-507, MacMilan Publishers.

Li et al., "Mg(OH)2@reduced Graphene Oxide Composite for Removal of Dyes From Water", Journal of Materials Chemistry, 2011, 21, 13765-13768, The Royal Society of Chemistry.

Li et al., "Preparation of Nanocomposites of Metals, Metal Oxides, and Carbon Nanotubes via Self-Assembly", J. Am. Chem. Soc., 2007, 129, 9401-9409, American Chemical Society.

Li et al., "Positively Charged Nanosheets Derived via Total Delamination of Layered Double Hydroxides", Chem. Mater., 2005, 17, 4386-4391, American Chemical Society.

Li et al., "Stable Platinum Nanoparticles on Specific MgAl2O4 Spinal Facets at High Temperatures in Oxidizing Atmospheres", Nature Communications, 2013, DOI: 10.1038/ncomms3481, MacMilan Publishers Limited.

Liu et al., "Layered Double Hydroxide Nano- and Microstructures Grown Directly on Metal Substrates and Their Calcined Products for Application as Li-Ion Battery Electrodes", Advanced Functional Materials, 2008, 18, 1448-1458, Wiley-VCH Verlag GmbH & Co.

Liu et al., "Gold-Catalyzed Direct Hydrogenative Coupling of Nitroarenes to Synthesize Aromatic Azo Compounds", Angew. Chem., 2014, 126, 7754-7758, Wiley-VCH Verlag GmbH & Co.

Liu et al., "Selective and Controlled Synthesis of a- and b-Cobalt Hydroxides in Highly Developed Hexagonal Platelets", J. Am. Chem. Soc., 2005, 127, 13869-13874, American Chemical Society.

Ma et al., "Metal-Organic Framework Derived Hybrd Co3O4-Carbon Porous Nanowire Arrays as Reversible Oxygen Evolution Electrodes", J. Am. Chem. Soc., 2014, 136, 13925-13931, American Chemical Society.

Makhluf et al., "Microwave-Assisted Synthesis of Nanocrystalline MgO and Its Use as a Bacteriocide", Adv. Funct. Mater., 2005, 15, 1708-1715, Wiley-VCH Verlag GmbH.

Mishra et al., "Effect of Nano-Mg(OH)2 on the Mechanical and Flame-Retarding Properties of Polypropylene Composites", Journal of Applied Polymer Science, 2004, 94, 116-122, Wiley Periodicals, Inc.

Nethravathi et al., "Synthesis and Anion-Exchange Reactions of a New Anionic Clay a-Magnesium Hydroxide", Journal of Colloid and Interface Science, 2011, 354, 793-797, Elsevier Inc.

Newman et al., "Comparative Study of Some Layered Hydroxide Salts Containing Exchangeable Interlayer Anions", Journal of Solid State Chemistry, 1999, 148, 26-40, Academic Press.

(56) References Cited

OTHER PUBLICATIONS

Nielsen et al., "Delamination, Synthesis, Crystal Structure and Thermal Properties of the Layered Metal-Organic Compound Zn(C12H14O4)", J. Mater. Chem., 2008, 18, 1002-1007, The Royal Society of Chemistry.

Ning et al., "Gas-Hydrate Formation, Agglomeration and Inhibition in Oil-Based Drilling Fluids for Deep-Water Drilling", Journal of Natural Gas Chemistry, 2010, 19, 234-240, Elsevier.

Oswald et al., "Bivalent Metal Hydroxides", Preparation and Crystal Growth of Materials with Layered Structures, 1977, 71-140.

Park et al., "Synthesis and Characterization of Al(OH)3/Polystyrene Nanocomposite Latex Particles by Emulsion Polymerization", Macromol. Symp., 2007, 247-250.

Pham et al., "A Silica-Supported Iron Oxide Catalyst Capable of Activating Hydrogen Peroxide at Neutral pH Values", Environ. Sci. Technol., 2009, 43, 8930-8935, American Chemical Society.

Pupovac et al. "Cu/MgAl2O4 as Bifunctional Catalyst for Aldol Condensation of 5-Hydroxymethylfurfural and Selective Transfer Hydrogenation", ChemSusChem, 2013, 6, 2103-2110.

Qian et al., "Micropore Modification of Zeolites with Transition-Metal Oxides", Colloids and Surfaces A: Physiochemical and Engineering Aspects, 2001, 180, 311-316, Elsevier Science B.V.

Rajamathi et al., "The Many Ways of Making Anionic Clays", Proc. Indian Acad. Sci. (Chem. Sci.), 2001, 5 & 6, 671-680, Indian Academy of Sciences.

Ramirez, A.P., "Colossal Magnetoresistance", J. Phys.: Condens. Matter, 1997, 9, 8171-8199, IOP Publishing Ltd.

Rao et al., "Synthesis of Complex Metal Oxides by Novel Routes", Acc. Chem. Res., 1987, 20, 228-235, American Chemical Society.

Rao, C.N.R., "Transition Metal Oxides", Annu. Rev. Phys. Chem., 1989, 40, 291-326, Annual Reviews Inc.

Raveau, B., "Transition Metal Oxides: Promising Functional Materials", Journal of the European Ceramic Society, 2005, 25, 1965-1969, Elsevier Ltd.

Reddy et al., "Metal Oxides and Oxysalts as Anode Materials for Li Ion Batteries", Chem. Rev. 2013, 113, 5364-5457, American Chemical Society.

U.S. Non-Final Office Action dated May 25, 2018, pertaining to U.S. Appl. No. 15/449,207.

Non-Final Office Action dated Apr. 23, 2018 pertaining to U.S. Appl. No. 15/449,347, filed Mar. 8, 2017.

Non-Final Office Action dated Jan. 5, 2018 pertaining to U.S. Appl. No. 15/453,106, filed Mar. 8, 2017.

\* cited by examiner

FIG. 6A                    FIG. 6B

SYNTHESIS OF MAGNESIUM ADAMANTANE SALTS AND MAGNESIUM OXIDE NANOCOMPOSITES, AND SYSTEMS AND METHODS INCLUDING THE SALTS OR THE NANOCOMPOSITES

CROSS-REFERENCE TO RELATED APPLICATIONS

This application claims the benefit of U.S. Provisional Application Ser. No. 62/309,657 filed Mar. 17, 2016, incorporated herein by reference.

BACKGROUND

Field

The present specification generally relates to magnesium diamondoid salts, nanocomposites containing magnesium oxide derived from the salts, to systems and methods including the salts or the nanocomposites, to polymer composites including the salts or the nanocomposites.

Abbreviations

° C.=Degrees Celsius
Å=Angstroms
ACA=1-adamantane carboxylic acid
AC=adamantine carboxylate
cm=centimeter ($10^{-2}$ meter)
EDX=Energy-dispersive X-ray
FWHM=full width at half maximum
h=hours
HRTEM=High-resolution transmission electron microscopy
IR=Infrared
LDH=layered double hydroxide
µm=micrometer ($10^{-6}$ meter)
mL=milliliter ($10^{-3}$ liter)
nm=nanometer ($10^{-9}$ meter)
PXRD=Powder X-ray diffraction
SEM=Scanning electron microscopy
TEM=Transmission electron microscopy
TGA=Thermogravimetric analysis
TMO=Transition metal oxide
wt. %=Weight percent

Technical Background

Brucite is a naturally occurring mineral and is characterized by a close packing of hydroxyl ions in which $Mg^{2+}$ ions occupy alternating layers of octahedral sites, leading to a stacking of charge-neutral metal hydroxide slabs of composition $[Mg(OH)_2]$. Each $Mg^{2+}$ ion is octahedrally surrounded by six $OH^-$ ions. The octahedra share edges to form infinite layers that are stacked, being stabilized by van der Waal's interactions. Potential exploitation of these hydroxides has been limited, because the materials exhibit: (1) limited interlayer chemistry; (2) low thermal stability; (3) a fixed layer composition; (4) no exfoliation.

Despite known limitations of the material, $Mg(OH)_2$ has many potential applications in the field of catalysis, sorption, and nanocomposites' for example. From a catalysis and sorption point of view, MgO should ideally have high surface area, thermal stability and reproducibility. Among all the bivalent divalent metal hydroxides, $Mg(OH)_2$ has an advantage over others because (a) it is cheap and economical, (b) it is easy to handle and (c) it is environmentally friendly. The immediate challenge for materials chemistry is to design and develop $\alpha\text{-}Mg(OH)_2/Mg(OH)_2$ based salts in which the crystals have large aspect ratios (length to thickness) of greater than 1000, high thermal stability, and an ability to form stable dispersions in various solvents.

Accordingly, significant need exists for synthetic methods that provide magnesium-based materials and composites of magnesium-based materials that are stable or dispersible and that enable control of size, shape, and activity of the crystals of the magnesium-based materials, particularly as precursors of reactive MgO. Further ongoing need exists for systems, methods, and composite materials that include the magnesium oxide/hydroxide materials.

SUMMARY

According some embodiments, a method for preparing a magnesium adamantane carboxylate salt is provided. The method includes mixing a magnesium salt and a diamondoid compound having at least one carboxylic acid moiety to form a reactant mixture. Further, the method includes hydrothermally treating the reactant mixture at a reaction temperature for a reaction time to form the magnesium adamantane carboxylate salt.

According to further embodiments, a method for preparing a nanocomposite is provided. The method includes thermally decomposing a magnesium adamantane carboxylate salt prepared according to embodiments of this disclosure to form the nanocomposite.

According to further embodiments, a catalyst system is provided. The catalyst system includes (a) a magnesium adamantane carboxylate salt prepared according to embodiments of this disclosure; (b) a nanocomposite prepared according to embodiments of this disclosure; or (c) a mixture of (a) and (b).

According to further embodiments, a method for catalyzing a chemical reaction between at least one first reactant and at least one second reactant is provided. The method includes reacting the at least one first reactant and at least one second reactant in the presence of a catalyst system according to embodiments of this disclosure.

According to further embodiments, a method for catalyzing the decomposition of a reactant is provided. The method includes decomposing the reactant in the presence of a catalyst system according to embodiments of this disclosure.

According to further embodiments, a polymer composite is provided. The polymer composite includes at least one polymer or copolymer and at least one filler material interspersed among the at least one polymer or copolymer to form a composite. The at least one filler material is chosen from: (a) a magnesium adamantane carboxylate salt prepared according to embodiments of the present disclosure; (b) a nanocomposite prepared according to embodiments of this disclosure; or (c) a mixture of (a) and (b).

According to yet further embodiments, a system for removing a chemical compound from a fluid stream is provided. The system includes an adsorbent chosen from: (a) a magnesium adamantane carboxylate salt prepared according to embodiments of the present disclosure, (b) a nanocomposite according to embodiments of the present disclosure, or (c) a mixture of (a) and (b). The system further includes a vessel in which or on which the chemical compound in the fluid stream is contacted with the adsorbent.

Additional features and advantages of the embodiments described in this specification will be set forth in the detailed description which follows, and in part will be readily apparent to those skilled in the art from that description or recognized by practicing the embodiments described in this specification, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described in this specification, and together with the description serve to explain the principles and operations of the claimed subject matter.

BRIEF DESCRIPTION OF THE DRAWINGS

FIG. 6A is an atomic-force micrograph of a selected area of an exfoliated Mg(0.5)-AC particle removed from a colloidal suspension.

FIG. 6B is a representation of the peak force errors in the micrograph of FIG. 6A.

DETAILED DESCRIPTION

Figure 1:
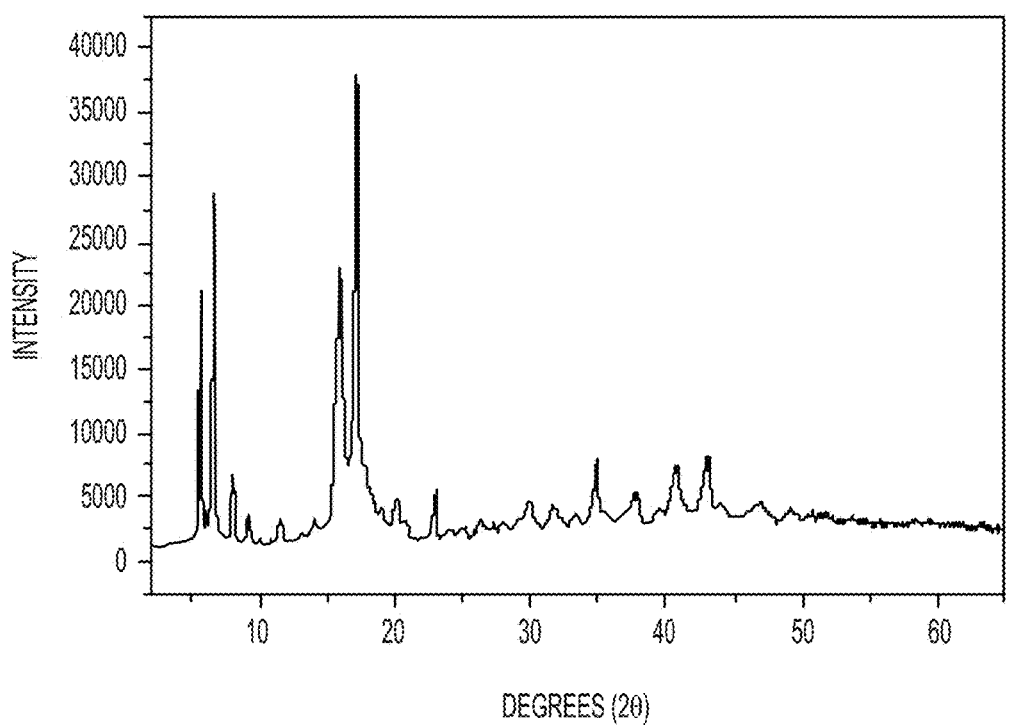
FIG. 1 is a powder x-ray diffraction (PXRD) pattern of a Mg(0.5)-AC magnesium adamantine carboxylate salt formed from $Mg(OH)_2$ and 1-adamantane carboxylic acid (ACA) with a 0.5:1 molar ratio of $Mg^{2+}$ to ACA.

The diamondoids and their derivatives have shown promise in various applications such as in supramolecular, petrochemical, and medicinal chemistry. Compounds prepared according to methods embodied in this specification unite the chemistries of magnesium oxides and diamondoids to form materials such as salts and nanocomposites incorporating magnesium or magnesium oxide. For example, in some embodiments, magnesium-adamantane carboxylate (Mg-AC) salts are synthesized and characterized. The synthesized Mg-AC shows a layered structure with large aspect ratio, high thermal stability, and the ability to disperse in various organic solvents. In other embodiments, the thermal decomposition of Mg-AC compounds provides nanocomposites composed of stable, sinter-free, microporous MgO supported on carbon. Further embodiments are directed to catalytic systems, catalytic methods, polymer composites, and adsorption systems each incorporating the Mg-AC compounds, the nanocomposites, or a combination of these.

As used in this specification, the term "diamondoid" refers to any chemical compound containing at least one adamantane moiety.

Reference will now be made in detail to embodiments of methods for preparing magnesium adamantane carboxylate salts and nanocomposites that are derived from the magnesium adamantane salts and contain magnesium oxide particles.

Methods for preparing a magnesium adamantine carboxylate salt include mixing a magnesium salt and a diamondoid compound having at least one carboxylic acid moiety to form a reactant mixture.

In the reactant mixture, the magnesium salt may be any magnesium compound containing $Mg^{2+}$ and a counteranion derived from an acid or a base. Non-limiting examples of magnesium salts, therefore, include $Mg(OH)_2$, $MgCl_2$, $MgBr_2$, $Mg(NO_3)_2$, and $MgSO_4$. In some embodiments, the magnesium salt may be $Mg(OH)_2$. MgO formed from the calcination of $Mg(OH)_2$ is of particular interest for its activity as a solid base catalyst.

In the reactant mixture, the diamondoid compound has at least one carboxylic acid moiety. In some embodiments, the at least one carboxylic acid is bonded to any non-bridgehead carbon atom of the diamondoid compound. In some embodiments, the diamondoid compound may be chosen from carboxylic acids of adamantane, diamantane, or triamantane. In some embodiments, the diamondoid compound may be adamantane 1-carboxylic acid (ACA).

The mixing of the magnesium salt and the diamondoid compound may be performed by any suitable method using any suitable apparatus to accomplish intimate mixing. For example, the mixing may be performed using solid-state techniques such as blending or grinding of dry powders. The mixing may be performed with the aid of an aqueous or organic solvent by combining powders and the solvent and subsequently stirring the resultant solution. Optionally, after such a wet mixing procedure, some or all of the solvent may be decanted or filtered from the resultant mixture before the magnesium salt and the diamondoid compound are placed under conditions suitable for their chemical reaction.

The methods for preparing a magnesium adamantine carboxylate salt further include hydrothermally treating the reactant mixture of the magnesium salt and the diamondoid compound at a reaction temperature for a reaction time to form the magnesium adamantane carboxylate salt. Hydrothermal treatment generally may include adding an aqueous solvent such as water to the reaction mixture, sealing the reaction mixture in a reaction vessel such as an autoclave, and heating the reaction vessel to the reaction temperature to cause crystallization of the magnesium adamantine carboxylate salt to occur in a high-pressure environment.

The reaction temperature is chosen to provide sufficient thermodynamic energy for the reaction of the magnesium salt and the diamondoid compound to proceed within the reaction vessel while also enabling crystallization of the magnesium adamantane carboxylate salt. The reaction temperature should be sufficiently high to enable the reaction to progress but also be sufficiently low to avoid decomposition of the adamantane carboxylate salt or solvation of crystallites. In some embodiments, the reaction temperature may be from 100° C. to 200° C., such as 100° C., 110° C., 120° C., 130° C., 140° C., 150° C., 160° C., 170° C., 180° C., 190° C., 200° C., or any other temperature between 100° C. and 200° C. Though in some embodiments the reaction temperature may be from 100° C. to 200° C., it is contemplated that other reactions may occur at temperatures less than 100° C. or greater than 200° C. In other embodiments, the reaction temperature may be from 100° C. to 150° C. or from 110° C. to 150° C. In one example, where magnesium salt is $Mg(OH)_2$, the reaction temperature may be 150° C.±10° C.

The reaction time is chosen to provide sufficient time for crystal growth and development of well-defined morphologies to occur as the magnesium adamantane carboxylate salt is formed at the reaction temperature. In some embodiments, the reaction time may be longer than 12 h, such as from 12 h to 72 h, from 24 h to 72 h, from 12 h to 48 h, or from 24 h to 48 h, for example. Though in some embodiments the reaction time may be longer than 12 h, it is contemplated that when higher reaction temperatures greater than 150° C. are chosen, for example, the reaction time may be shorter than 12 h.

The methods for preparing a magnesium adamantane carboxylate salt may further include customary isolation steps such as cooling or depressurizing the reaction vessel, removing the reaction mixture from the reaction vessel, removing solvent from the reaction mixture by filtering or any other suitable technique, washing the magnesium adamantane carboxylate salt with an aqueous or organic solvent that does not dissolve the magnesium adamantane carboxylate salt, drying the magnesium adamantane carboxylate salt, or any combination of these steps. In some embodiments, the magnesium adamantane carboxylate salt may be vacuum filtered from any solvent present in the reaction vessel, washed with water, and dried at a suitable temperature for a suitable time. For example, the magnesium adamantane carboxylate salt may be dried at 65° C. for 24 h to drive off residual solvent from the hydrothermal treatment.

The magnesium adamantane carboxylate salt prepared using a magnesium salt and ACA will be subsequently described by a shorthand notation Mg(x)-AC, where x is the ratio of $Mg^{2+}$ to ACA in the reaction mixture used to prepare the magnesium adamantane salt, and AC represents the carbon support derived from the adamantane carboxylate moiety of the ACA. For example, Mg(0.5)-AC represents a magnesium adamantane carboxylate salt prepared by reacting $Mg(OH)_2$ and ACA with a 0.5:1 molar ratio of $Mg^{2+}$ to ACA. Likewise, Mg(1.0)-AC represents a magnesium adamantane carboxylate salt prepared by reacting $Mg(OH)_2$ and ACA with a 1.0:1 molar ratio of $Mg^{2+}$ to ACA.

In some embodiments, the reaction mixture may be prepared by mixing a magnesium salt such as, for example, $Mg(OH)_2$, and ACA in amounts that provide a ratio of $Mg^{2+}$ to ACA in the reaction mixture of from 0.5:1 to 1.0:1. The specific ratio of $Mg^{2+}$ to ACA in the reaction mixture may be chosen to affect the overall crystal morphology of the magnesium adamantane carboxylate salt to a desired form. Without intent to be bound by theory, it is believed that the crystal morphology of the magnesium adamantane carboxylate salt may be tailored by increasing or decreasing the ratio of $Mg^{2+}$ to ACA in the reaction mixture. Though in some embodiments the ratio of $Mg^{2+}$ to ACA may be selected from 0.5:1 to 1.0:1, it is contemplated that the crystal morphology of the magnesium adamantane carboxylate salt may be further tailored by decreasing the ratio of $Mg^{2+}$ to ACA to less than 0.5:1 or by increasing the ratio of $Mg^{2+}$ to ACA to greater than 1.0:1. Even so, a point of magnesium saturation is believed to exist, such that at a ratio of $Mg^{2+}$ to ACA greater than the saturation point additional magnesium ions cannot be incorporated into the magnesium adamantane carboxylate salt.

The Mg-AC compounds may exhibit a layered structure or morphology. In some embodiments, the layered structure or morphology Mg-AC compounds may manifest as a plurality of layers lacking edge-to-face connections. The plurality of layers may be composed of individual layers each having an aspect ratio greater than 500 or greater than 1000. That is, each of the individual layers may have a length measurement that is at least 500 times or at least 1000 times as long as a thickness measurement of the same layer. For example, the layer may have a length of 10 μm to 20 μm and a thickness of 10 nm to 20 nm. These very thin layers may in turn exhibit exfoliation, particularly in the presence of certain solvents. The Mg-AC material also may form stable dispersions or gels in various solvents such as polar organic solvents. For example, Mg-AC layers may exfoliate in organic solvents such as ethanol and acetone. Without intent to be bound by theory, it is believed that the presence of high-aspect ratio layers that exfoliate in Mg-AC may benefit the overall properties of materials such as polymer nanocomposites in which the Mg-AC is used as a filler.

Further embodiments of this specification are directed to methods for preparing nanocomposites. The methods for preparing the nanocomposites include thermally decomposing a magnesium adamantane carboxylate salt prepared according to the methods previously described in this specification. In some embodiments, the nanocomposites include magnesium oxide particles or structures supported on a carbon framework derived from the diamondoid compound.

In some embodiments for preparing nanocomposites, thermally decomposing the magnesium adamantane carboxylate salt may include heating the magnesium adamantane carboxylate salt. The heating of the magnesium adamantane carboxylate salt may be conducted, for example, in air at a decomposition temperature for a decomposition time. The decomposition temperature and the decomposition time may be selected to result in complete decomposition of the magnesium adamantane carboxylate salt. Complete decomposition of the magnesium adamantane carboxylate salt may include conversion of any magnesium hydroxide functionalities in the adamantane carboxylate salt to magnesium oxide particles. Suitable decomposition temperatures may be greater than 200° C., greater than 300° C., greater than 400° C., or greater than 500° C., for example. The decomposition time may be chosen as any time sufficient to result in complete decomposition of the magnesium adamantane carboxylate salt at the chosen decomposition temperature. For example, the decomposition time may be longer than 1 hour, such as 2 hours, 3 hours, 4 hours, or longer than 5 hours. In example embodiments, magnesium adamantane carboxylate salts formed from $Mg(OH)_2$ and ACA may decompose fully at a decomposition temperature of about 450° C. and a decomposition time of at least 4 hours.

Nanocomposites formed by thermally decomposing the magnesium adamantine carboxylate salts may exhibit a variety of crystal morphologies that may depend on variables such as the ratio of magnesium salt to diamondoid compound in the reaction mixture used to form the magnesium adamantane carboxylate salt, the reaction time and temperature used to form the magnesium adamantine carboxylate salt, and the decomposition conditions used to form the nanocomposite itself.

In some embodiments, the methods for preparing nanocomposites include thermally decomposing magnesium adamantane carboxylate salts prepared by reacting $Mg(OH)_2$ and ACA. Nanocomposites formed from such magnesium adamantane carboxylate salts may include magnesium oxide particles (MgO) of a particular shape or morphology dispersed on a carbon support of a particular shape or morphology. The metal-oxide particle may be spherical, rectangular, ribbon-like, or in the form of nanowires, nanorods, or nanowhiskers, for example. The magnesium oxide particles may have particle sizes from 10 nm to 20 nm, for example. Likewise, the carbon support may exhibit a morphology such as a sheet, a nanorod, a nanowire, or a nanowhisker.

In some embodiments, the magnesium oxide particles may be uniformly dispersed over a surface of a carbon support derived from the adamantane moieties of the magnesium adamantane carboxylate salt. The weight fraction of MgO particles and carbon support may vary in the nanocomposite, depending on the conditions used to prepare the nanocomposite. In some embodiments, the nanocomposite may include from 50 wt. % to 90 wt. % MgO particles and from 10 wt. % to 50 wt. % carbon, based on the total weight of the nanocomposite. For example, the nanocomposite may include from 70 wt. % to 80 wt. % MgO particles and from 20 wt. % to 30 wt. % carbon, based on the total weight of the nanocomposite.

Further embodiments of this specification are directed to catalyst systems. The catalyst systems may include (a) a magnesium adamantane carboxylate salt prepared according to any embodiment previously described; (b) a nanocomposite such as magnesium oxide particles supported on carbon prepared according to any embodiment previously described, such as by thermal decomposition of a magnesium adamantane carboxylate salt; or (c) any catalytically active mixture of (a) and (b).

Accordingly, further embodiments of this specification are directed to methods for catalyzing a chemical reaction between at least one first reactant and at least one second reactant. Such methods may include reacting the at least one first reactant and at least one second reactant in the presence of a catalyst system described previously. The at least one first reactant and the at least one second reactant may be any chemical compounds, the chemical reaction of which is catalytically facilitated, such as by being made thermodynamically possible or more favorable, or kinetically influenced by the presence of the magnesium adamantane carboxylate salt or the MgO nanocomposite separately or in combination.

Still further embodiments of this specification are directed to methods for catalyzing the decomposition of a reactant. Such methods may include decomposing the reactant in the presence of a catalyst system described previously. The decomposing of the reactant may be conducted under milder conditions than those generally known to decompose the reactant, such as under a decreased decomposition temperature, a decreased decomposition time, or a decreased decomposition pressure.

Still further embodiments of this specification are directed to polymer composites that contain at least one polymer or copolymer in combination with at least one filler compound interspersed among the at least one polymer or copolymer to form a composite. In such embodiments, the at least one filler compound may be chosen from (a) a magnesium adamantane carboxylate salt prepared according to any embodiment previously described; (b) a nanocomposite such as magnesium oxide particles supported on carbon prepared according to any embodiment previously described, such as by thermal decomposition of a magnesium adamantane carboxylate salt; or (c) any mixture of (a) and (b).

Still further embodiments of this specification are directed to systems for removing a chemical compound from a fluid stream such as a liquid stream, a gas stream, or a slurry containing a liquid and a solid. The systems may include an adsorbent chosen from: (a) a magnesium adamantane carboxylate salt prepared according to any embodiment previously described; (b) a nanocomposite such as magnesium oxide particles supported on carbon prepared according to any embodiment previously described, such as by thermal decomposition of a magnesium adamantane carboxylate salt; (c) a polymer composite according to any embodiment previously described; or (d) any mixture of (a), (b), and (c). The systems may further include any suitable vessel in which, or any active surface on which, the chemical compound in the fluid stream is contacted with the adsorbent so as to be adsorbed onto the adsorbent and removed from the fluid stream.

Thus, embodiments of magnesium diamondoid salts, nanocomposites of carbon-supported magnesium oxide particles have been described, along with further embodiments of catalytic systems and methods, polymer composites, systems for removing chemical compounds from fluid streams, and drilling fluids incorporating one or more of the magnesium diamondoid salts or nanocomposites. In example embodiments, 1-adamantane carboxylate was used as a structure directing agent to generate the magnesium compounds having varied morphologies. The thermal decomposition or calcination of Mg-AC compounds results in an in situ generation of carbon-supported magnesium oxides that may show high catalytic and thermal stability compared to conventional nano-MgO.

EXAMPLES

The embodiments described in this specification will be further clarified by the following Examples. It should be understood that the following Examples are not intended to limit the scope of this disclosure or its claims to any particular embodiment.

Example 1

Synthesis and Physical Characterization of Mg(0.5)-Adamantane Carboxylate Salt

Mg-adamantane (Mg-AD) compounds were hydrothermally synthesized by mixing $Mg(OH)_2$ and 1-adamantane carboxylic acid (ACA) in amounts to provide a 1:2 molar ratio of $Mg^{2+}$ to ACA to form a reaction mixture, then transferring the reaction mixture to a Teflon-lined stainless-steel autoclave and heating the reaction mixture at 150° C.

for 24 h. The reactants were mixed by stirring for 1 h on a magnetic stirrer. The resultant product, Mg(0.5)-AC (where 0.5 refers to the original $Mg^{2+}$-to-ACA mixing ratio and "AC" refers to adamantane carboxylate) was vacuum filtered, washed with a copious amount of water, and then dried at 65° C. for 24 h. Products were characterized by powder X-ray diffraction (PXRD), infra-red (IR) spectroscopy, scanning electron microscopy (SEM), thermo gravimetric analysis (TGA), atomic force microscopy (AFM), and transmission electron microscopy (TEM).

The Mg(0.5)-AC was analyzed by PXRD. The PXRD spectrum in FIG. 1 exhibited a series of basal reflections at 2θ angles of 5.7°, 6.6°, 8.0°, 9.2°, and 11.5°, corresponding to d-spacings of 15.41 Å, 13.3 Å, 11.0 Å, 9.6 Å, and 7.7 Å, respectively. Strong reflections occur centered around 2θ angles of 15° to 17°, and several low to medium intensity reflections appeared in the 2θ range 30° to 50°. In addition, low-intensity twin reflections occurred in the 2θ range 57° to 60°. All of these features in the PXRD pattern indicate the formation of a material with a layered structure.

Figure 2:
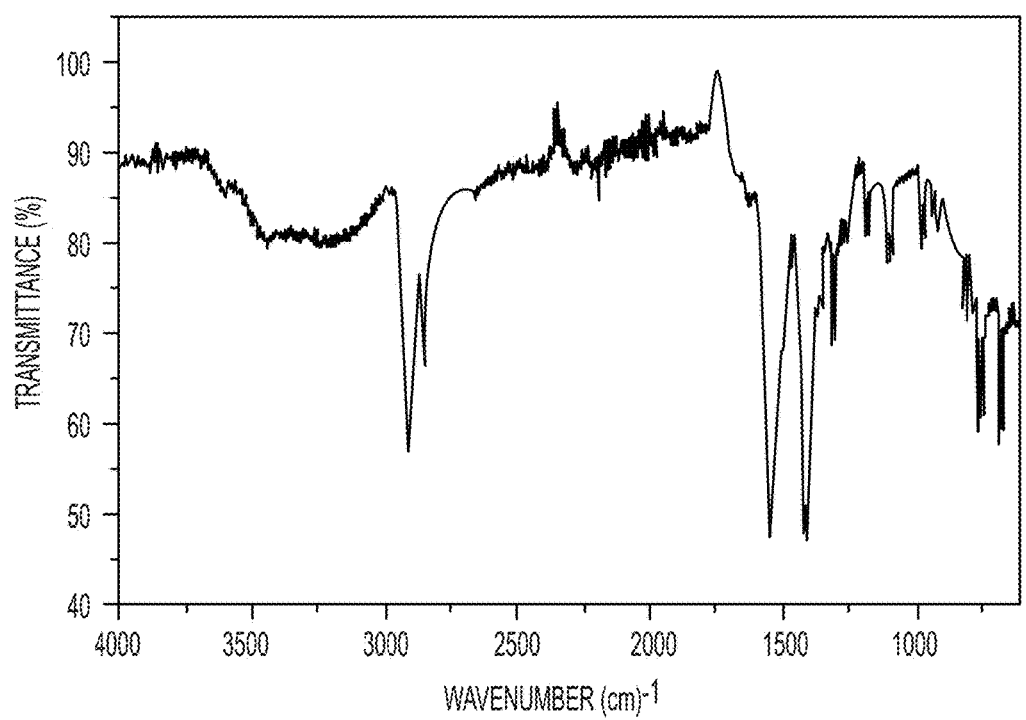
FIG. 2 is an infrared (IR) spectrum of a Mg(0.5)-AC magnesium adamantane carboxylate salt formed from $Mg(OH)_2$ and 1-adamantane carboxylic acid (ACA) with a 0.5:1 molar ratio of $Mg^{2+}$ to ACA.

The Mg(0.5)-AC was further characterized with IR spectroscopy. The IR spectrum in FIG. 2 shows the symmetric and antisymmetric stretching vibrations of the $COO^-$ group at 1411 $cm^{-1}$ and 1550 $cm^{-1}$ respectively. The vibrations at 2900 $cm^{-1}$ and 2847 $cm^{-1}$ arise from the C—H bonds of the adamantane carboxylate ion. The broad vibration in the range of 3200 $cm^{-1}$ to 3400 $cm^{-1}$ arises from the hydrogen-bonded hydroxyl ion. The small shoulder at about 3600 $cm^{-1}$ arises from the non-hydrogen bonded hydroxyl ion and is believed to indicate a small amount of precursor $Mg(OH)_2$ in the resultant product as an impurity. The medium intensity vibrations less than 1000 $cm^{-1}$ arise from the bending and stretching of metal-oxygen bonds.

Figure 3:
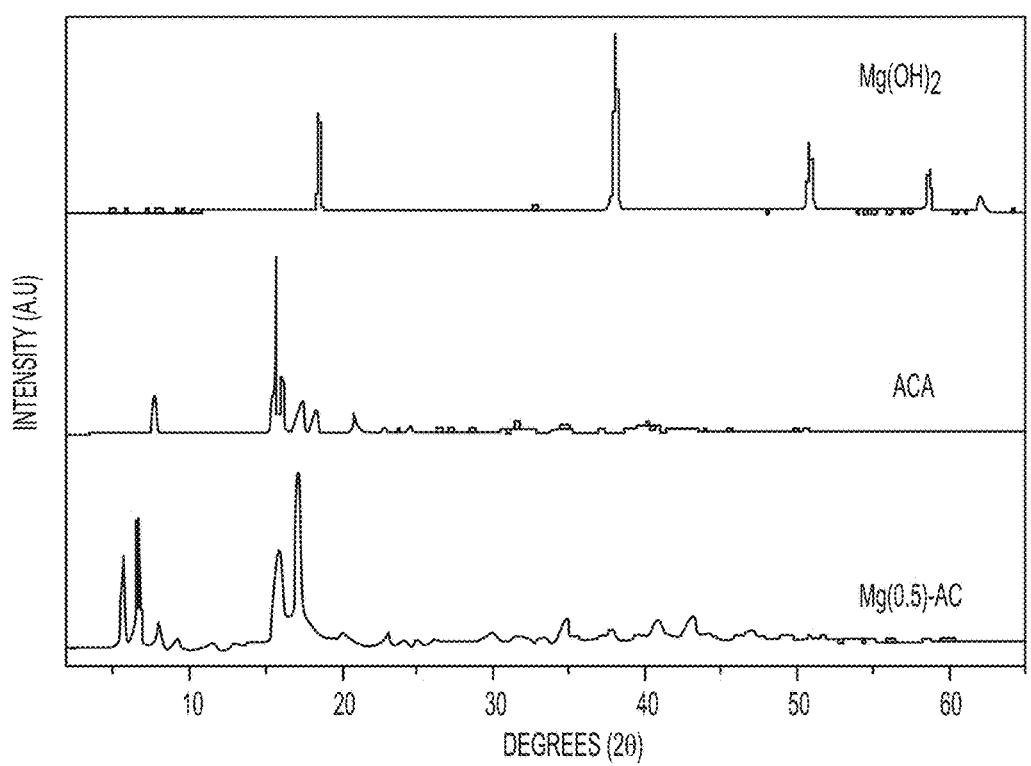
FIG. 3 includes stacked IR spectra of $Mg(OH)_2$, ACA, and Mg(0.5)-AC.

Comparison of starting materials with the Mg(0.5)-AC was undertaken to check the possible impurities and unreacted starting materials. FIG. 3 shows overlaid PXRD patterns of Mg(0.5)-AC, ACA, and $Mg(OH)_2$. The Mg(0.5)-AC has a set of reflections that do not correspond with those of the starting materials, except a low intensity reflection at 37.9° arising from starting $Mg(OH)_2$, which was also confirmed by IR analysis. The twin peaks of ACA (100% intensity) in the 2θ range of 15° to 17° are in the Mg(0.5)-AC as well. The peak positions and full width at half maxima (FWHM) shows that the peaks are shifted in Mg(0.5)-AC more than 1° and are broadened. This precludes the possibility of the starting ACA being present in the Mg(0.5)-AC.

Figure 4:
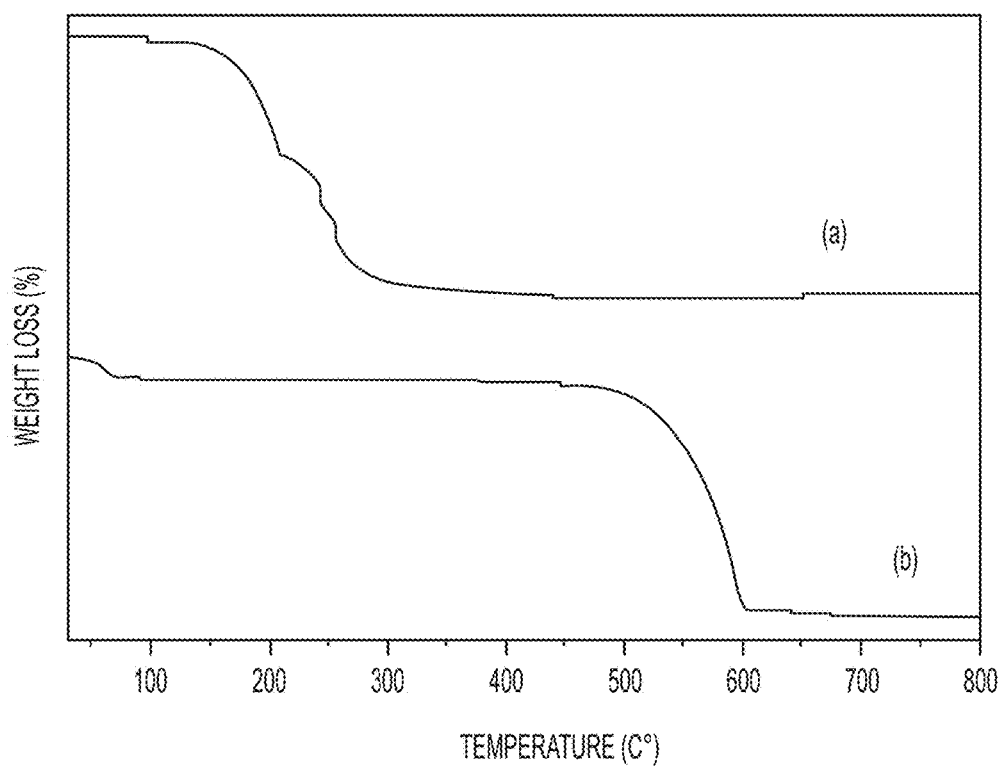
FIG. 4 includes stacked thermogravimetric analyses of (a) ACA; and (b) Mg(0.5)-AC.
Figure 5A:
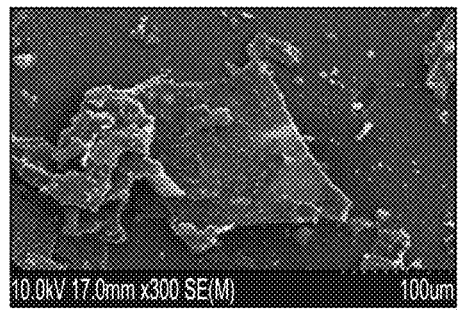
FIGS. 5A-5D are SEM micrographs at various magnifications of Mg(0.5)-AD prepared according to embodiments of this specification.
Figure 5B:
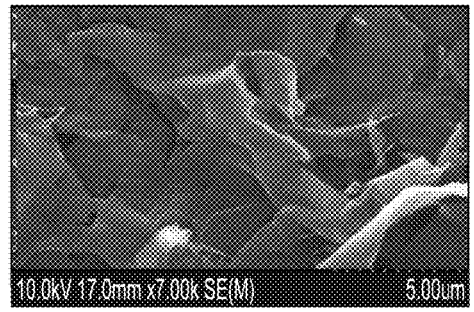
Figure 5C:
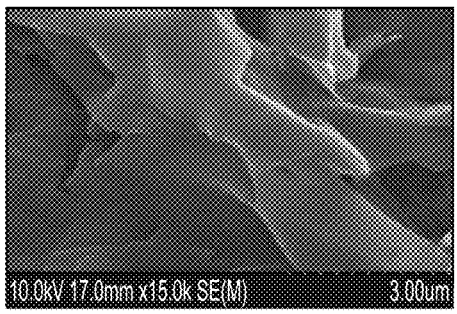
Figure 5D:
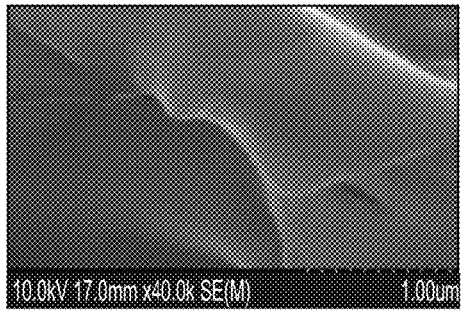

Thermal decomposition behavior of newly formed Mg(0.5)-AC was studied by thermogravimetric analysis (TGA) in a helium gas atmosphere from 30° C. to 800° C. at a heating rate of 10° C./min. The Mg(0.5)-AC shows a two-step mass loss, as shown in plot (b) of FIG. 4. The 5 wt. % to 6 wt. % mass loss around 60° C. may be attributable to adsorbed water. The TGA evidences that the compound is stable up to 450° C. and losses around 85 wt % of its mass in the range of 450° C. to 600° C. The mass loss in this range is attributable to loss of the adamantane carboxylate moiety and hydroxyl ions. The residue is only around 10 wt. %, indicating the formation of highly porous nanoscale MgO. The single step mass loss, except the loss of adsorbed water confirms the single-phase nature of the Mg(0.5)-AC. In contrast and as illustrated in plot (a) of FIG. 4, the starting ACA shows entirely different thermal behavior. Adamantane carboxylic acid was found to be stable up to 100° C. and to decompose completely in a single step between 120° C. and 300° C. Without intent to be bound by theory, it is believed that the unusually high thermal stability of the Mg(0.5)-AC may arise from the formation of $Mg^{2+}$-adamantane carboxylate ion bonding.

The morphology and nature of the Mg(0.5)-AC was further characterized by SEM. The SEM images of Mg(0.5)-AC in FIGS. 5A-5D at various magnifications evidence a layered morphology. The layers have very large aspect ratios, with dimensions of several microns in length and thickness of several nanometers. The layers are stacked one above the other and do not appear to have edge-to-face sharing connections that are common for many types of layered solids have. The absence of edge-to-face sharing connections in the Mg(0.5)-AC may indicate that the Mg(0.5)-AC can be easily exfoliated.

Example 2

Dispersion and Exfoliation of Mg(0.5)-Adamantane Carboxylate Salt

Based on its physical characterizations, the Mg(0.5)-AC has been found to be a layered structure with high aspect ratio and high thermal stability. Therefore, the Mg(0.5)-AC is believed to have all the qualities to become a good filler material for various nanocomposites. To check the suitability of Mg(0.5)-AC to blend with various polymers and ability to form dispersions, various polar and nonpolar solvents were used. The dispersion studies were carried out by using six different solvents with a variety of physical properties. Dispersion studies of the product in various solvents were carried out on 100 mg of Mg(0.5)-AC in 100 mL of various solvents to form a suspension that was stirred for 24 h on a magnetic stirrer. The results of the study are tabulated in TABLE 1.

TABLE 1

| Solvent | Solvent Type | Dispersion Characteristic |
| --- | --- | --- |
| Water | Polar | No dispersion |
| Ethanol | Polar | Stable dispersion |
| Tetrahydrofuran | Polar | Stable dispersion |
| N,N-Dimethylformamide | Polar | Stable gel |
| 1,4-Dioxane | Polar | Stable dispersion |
| Pentane | Nonpolar | No dispersion |

The Mg(0.5)-AC did not show any exfoliation or any kind of dispersion with water, indicating the hydrophobic nature of compound. When a polar organic solvent such as ethanol was used, the Mg(0.5)-AC formed a dispersion within 30 min. The Mg(0.5)-AC dispersed in 1,4-dioxane and formed a stable gel with N,N-dimethyl formamide. The Mg(0.5)-AC was found to form a stable dispersion with widely used tetrahydrofuran (THF). This shows that Mg(0.5)-AC has ability to form stable dispersions with polar organic solvents and can be used as filler in various nanocomposites involving organic polymers. On the other hand, the Mg(0.5)-AC did not show any exfoliation with nonpolar pentane.

The exfoliation of layered solids has great importance in materials chemistry generally. Exfoliated layers have been observed in various hybrid materials such as polymer based nanocomposites. The size and shape of the exfoliated layers determines the properties of the hybrid materials. Generally, exfoliation results in the formation of smaller tactoids having a thickness of nanometers, which in turn increases the surface area of the material. At the same time, exfoliation greatly reduces the lateral dimensions of the layers and is not ideal for polymer nanocomposites. The shearing forces involved in the exfoliation tend to destroy the lateral dimensions of the layered solids.

Figure 6C:
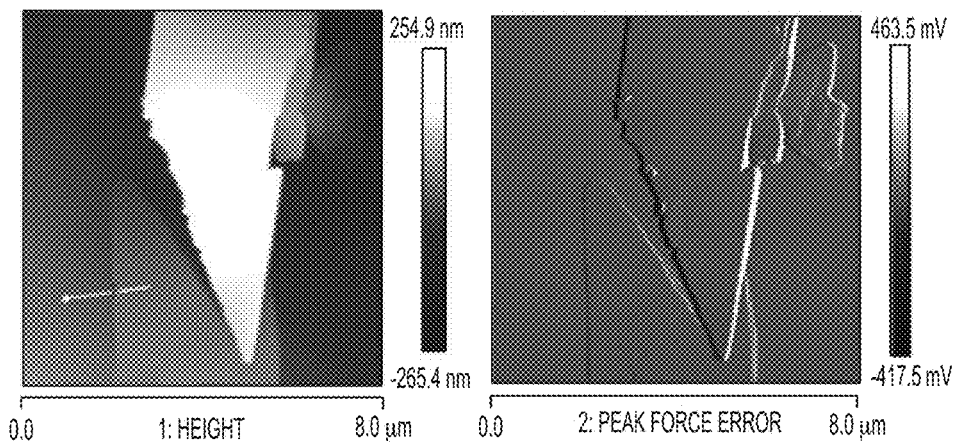
FIG. 6C is a graph of height profile in the exfoliated particle, measured across the path indicated in FIG. 6A.
Figure 6C:
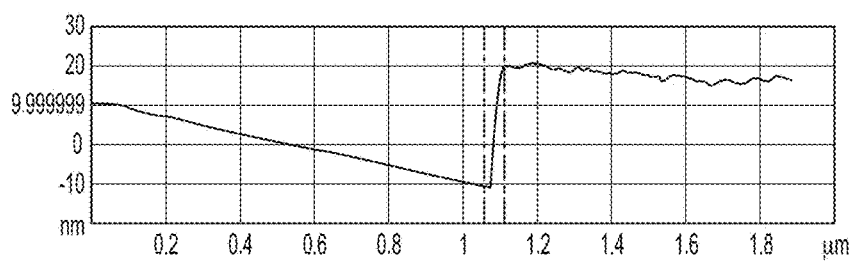

The exfoliated Mg(0.5)-AC colloidal suspensions were characterized by AFM to see the extent of exfoliation. FIG. 6A shows the topological profile of a selected area of an exfoliated Mg(0.5)-AC particle removed from a colloidal ethanol suspension of Mg-AC particles. FIG. 6B shows the peak-force errors in the same measurement. FIG. 6C is a height profile of the particle, measured along the path indicated in FIG. 6A. The exfoliated samples show the layers having thickness of 10 nm to 20 nm and a lateral dimension greater than 10 µm. These dimensions are equivalent to an aspect ratio of from 500 to 1000.

Example 3

Effect of Mg Supersaturation on Phase Formation and Morphology

The supersaturation of the initial reaction mixture plays a crucial role in phase formation of any material. The Mg(0.5)-AC prepared in Example 1 had a $Mg^{2+}$/ACA ratio of 1:2. To characterize the effect of $Mg^{2+}$/ACA ratio on the Mg-adamantane carboxylate phase formation, Mg(1.0)-AC was prepared by the same synthetic route as described in Example 1, except that the initial reactants were mixed to provide a $Mg^{2+}$/ACA ratio of 1:1. Thus, the Mg(1.0)-AC was prepared with a larger molar fraction of $Mg^{2+}$ compared to the Mg(0.5)-AC of Example 1.

Figure 7:
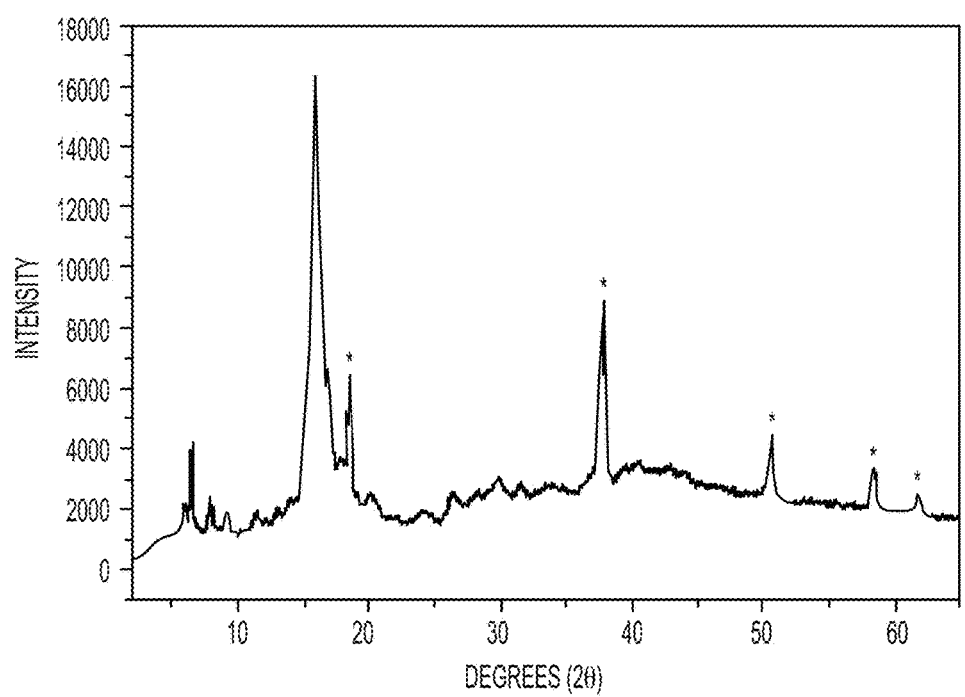
FIG. 7 is PXRD pattern of a Mg(1.0)-AC magnesium adamantane salt formed from $Mg(OH)_2$ and 1-adamantane carboxylic acid (ACA) with a 1.0:1 molar ratio of $Mg^{2+}$ to ACA. * indicates brucite impurity.
Figure 8A:
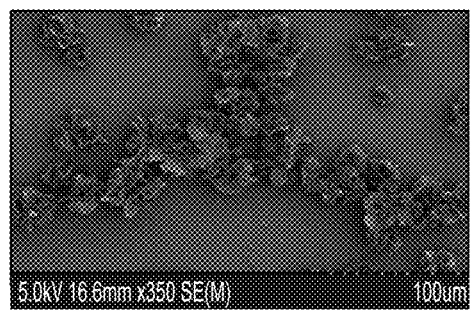
FIGS. 8A-8D are SEM micrographs at various magnifications of Mg(1.0)-AC nanocomposite prepared according to embodiments of this specification.
Figure 8B:
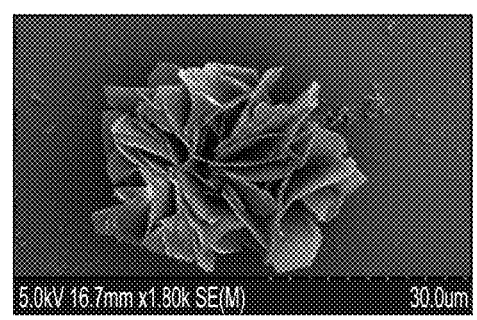
Figure 8C:
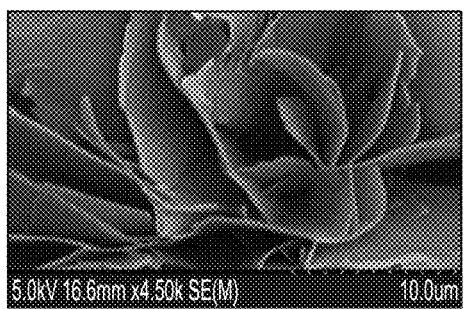
Figure 8D:
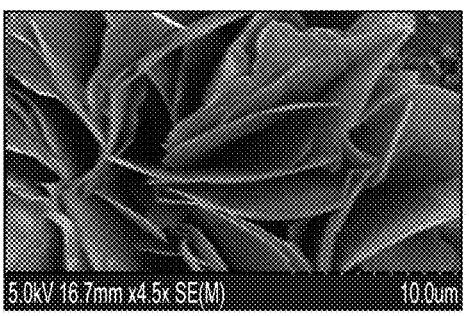

The PXRD pattern of the Mg(1.0)-AC in FIG. 7 retains all the reflections corresponding to Mg-AC, as compared to the PXRD of Mg(0.5)-AC (FIG. 1). In addition, the Mg(1.0)-AC PXRD spectrum shows several high intensity reflections (marked with *) believed to arise from unreacted $Mg(OH)_2$. The appearance of unreacted starting material in the Mg(1.0)-AC illustrates that stoichiometric ratio of the starting materials $Mg(OH)_2$ and ACA affects whether or not the resulting Mg-AC material will be a single phase material.

The Mg(1.0)-AC was further characterized with SEM to ascertain the effect of $Mg^{2+}$/ACA on the morphology of the material. FIGS. 8A-8D are SEM images of Mg(1.0)-AC at various magnifications. The morphology of Mg(1.0)-AC appears to be different from that of Mg(0.5)-AC. Though the SEM of Mg(1.0)-AC shows the layered morphology with large layers as with Mg(0.5)-AC, the crystallites of Mg(1.0)-AC appear to be connected through edge-to-face sharing, giving rise to a sand-flower morphology. Thus, by changing the concentration of $Mg^{2+}$ and ACA in the starting reaction mixture, it is possible to provide Mg-AC with a different morphology and orientation. In addition to the Mg-AC phase, the SEM of Mg(1.0)-AC also shows aggregated, featureless particles of unreacted $Mg(OH)_2$. In view of these morphological differences, the two compounds, Mg(0.5)-AC and Mg(1.0)-AC, are expected to show different behaviors.

Example 4

Effect of Magnesium Source on Mg-Adamantane Carboxylate Salt Formation

Similar to the supersaturation, the nature of initial reactants play a crucial role in deciding the formation of a compound. In this particular case, the source of $Mg^{2+}$ could be a deciding factor in formation of the Mg-AC. In a separate experiment, $Mg(NO_3)_2$ was used as a source of Mg, in place of $Mg(OH)_2$ and was reacted with ACA as in Example 1.

The PXRD of the resultant compound formed using $Mg(NO_3)_2$ as the magnesium source shows reflections corresponding to ACA, except for two weak reflections corresponding to d-spacings of 17.07 Å and 15.65 Å. The pH of the filtrate was found to be about 4, in contrast to the pH of about 9 present in the reactant mixtures used to form Mg(0.5)-AC in Example 1 and Mg(1.0)-AC in Example 3. The peak at 15.65 Å is similar to the one observed in Mg(0.5)-AC, but other reflections are absent including the high intensity peaks. This shows the crucial role of nature of the initial reactants and pH on the formation of Mg-adamantane carboxylate compound.

Example 5

MgO Nanocomposites from Thermal Decomposition of Mg(0.5)-AC and Mg(1.0)-AC

On calcination, the Mg-AC compounds generate MgO supported on carbon. MgO is a basic oxide and has the potential to be a good catalyst and a good sorbent for various acidic gases. In general, MgO formed or supported by other techniques has known fundamental limitations such as low surface area, low thermal stability, and agglomeration upon cycling. MgO formed by decomposition of Mg-AC compounds described in this specification are expected to overcome some of these limitations by generating macroporous carbon/adamantane chains with dispersed MgO in a one pot synthesis.

Figure 9:
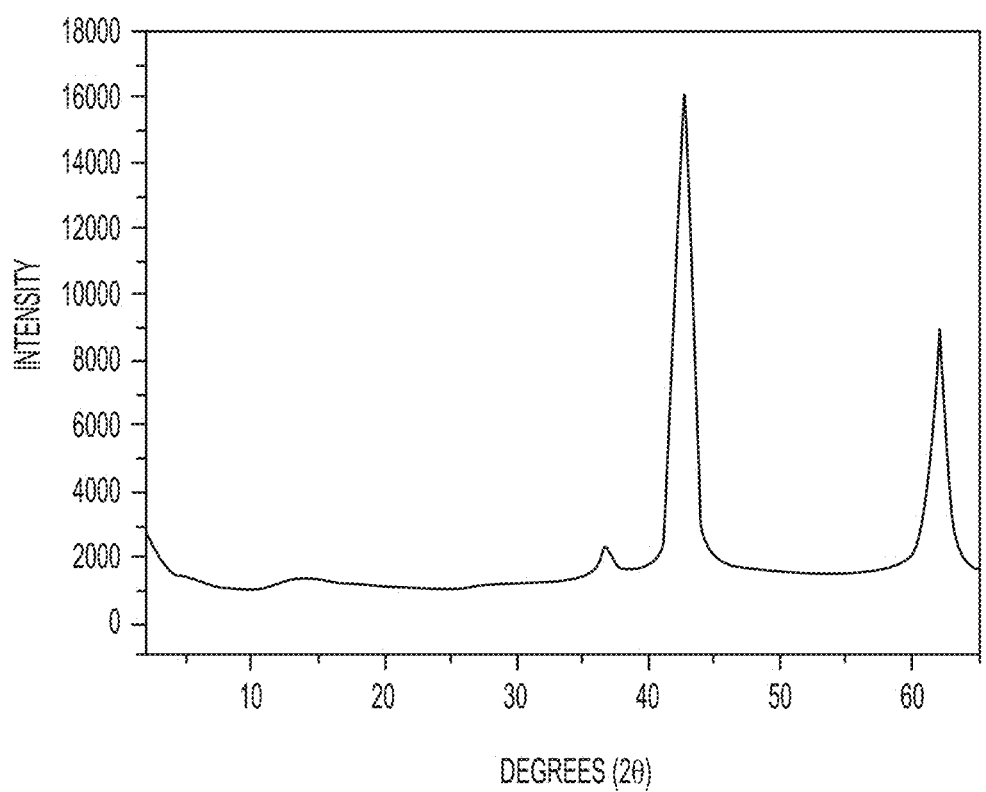
FIG. 9 is a PXRD pattern of a nanocomposite prepared by thermally decomposing Mg(0.5)-AC.
Figure 10A:
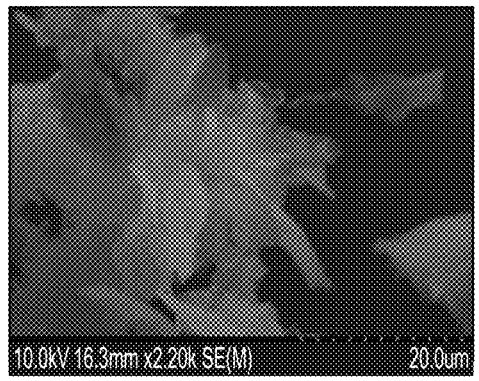
FIGS. 10A-10D are SEM micrographs at various magnifications of the nanocomposite prepared by thermally decomposing Mg(0.5)-AC.
Figure 10B:
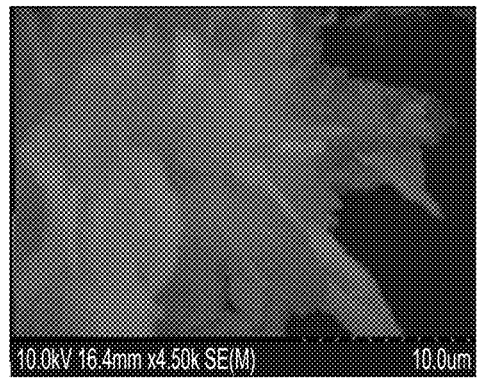
Figure 10C:
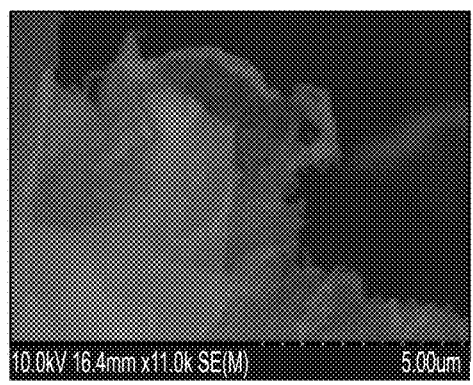
Figure 10D:
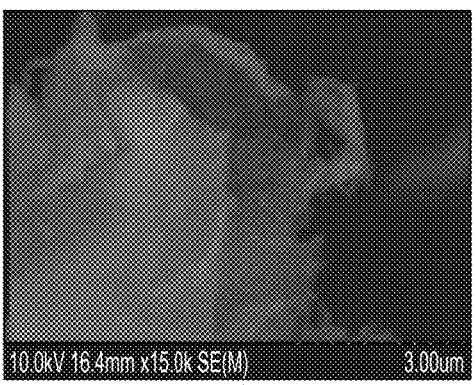

The Mg(0.5)-AC of Example 1 was thermally decomposed in a muffle furnace from room temperature to 450° C. in air atmosphere (5° C./min). The PXRD pattern of the resultant material in FIG. 9 shows reflections consistent with literature values for MgO at 2θ values of 37.1°, 43.03°, and 62.2°, corresponding to d-spacings of 2.42 Å, 2.1 Å, and 1.49 Å, respectively. It is believed that the broad hump centered around 14° is not attributable to MgO and likely originates from long-chain carbon atoms of the adamantane moiety.

The material obtained from decomposition of Mg(0.5)-AC was further characterized by SEM. In the micrographs at various magnifications in FIGS. 10A-10D, the resultant MgO nanocomposite has a sheet like morphology with large micropores. The sheets are very thin and have micron-sized dimensions. This sheet-like morphology can be attributed to the adamantane moiety working as a template for growing MgO in this fashion and also prevented the agglomeration of the crystallites.

To validate the presence of adamantane/carbon moiety in the sample, EDX was performed. To avoid the interference of substrate carbon with the sample, a silicon wafer was used as a substrate to record EDX spectra. The EDX spectra showed peaks from carbon, oxygen, and magnesium, indicating the presence of carbon from the adamantane in the sample. Peaks from gold were observed, corresponding to Au/Pd used for coating the sample. Elemental mapping performed to determine the distribution of the carbon in the sample. The elemental mapping showed a uniform distribution of carbon, along with magnesium and oxygen throughout the sample. This confirms the presence and role of adamantane in synthesizing supported metal oxides with large-aspect ratio and micropores.

Figure 11A:
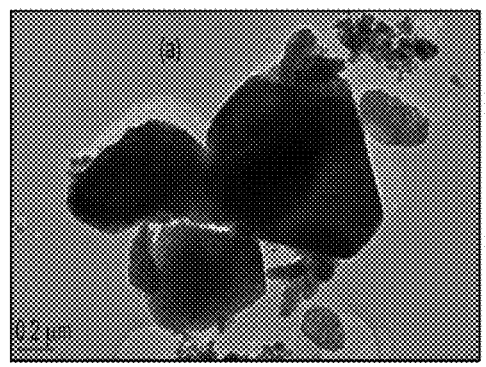
FIGS. 11A and 11B are bright-field transmission electron micrographs at various magnifications of the nanocomposite prepared by thermally decomposing Mg(0.5)-AC.
Figure 11B:
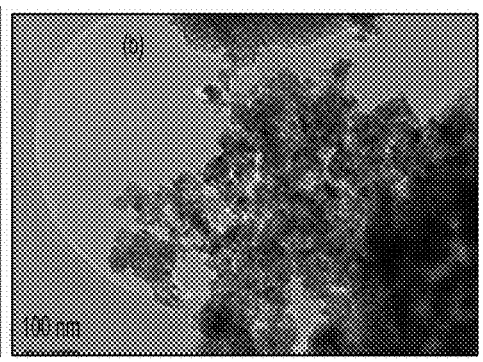
Figure 11C:
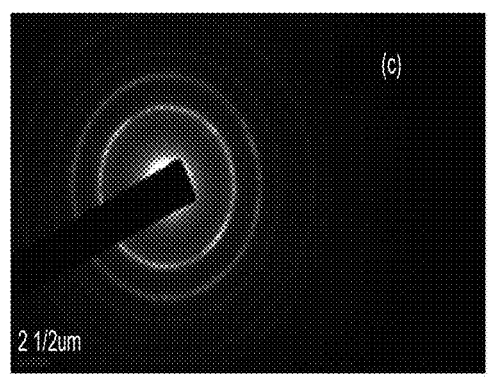
FIG. 11C shows an electron diffraction pattern of the nanocomposite prepared by thermally decomposing Mg(0.5)-AC.
Figure 11D:
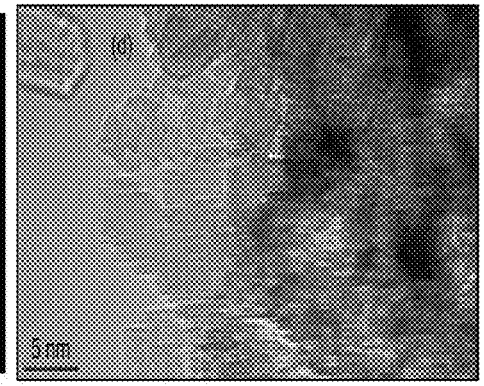
FIG. 11D shows a high-magnification HRTEM image of the nanocomposite prepared by thermally decomposing Mg(0.5)-AC.

High-resolution transmission electron microscopy (HR-TEM) was used to calculate the crystallite size and phase identification of the MgO formed. The bright-field TEM images in FIGS. 11A and 11B show the formation of MgO in large sheets having high porosity. The average size of the crystallites, as determined from the high-magnification HRTEM image of FIG. 11D were found to be in the range of 5 nm to 10 nm. The electron diffraction pattern of FIG. 11C further confirms the MgO phase. Reactivity of MgO generally is known to depend on size, shape, and synthesis method used to form the MgO. The smaller the size, the better the expected activity and selectivity, owing to larger surface areas and more synergistic bonding.

Figure 12:
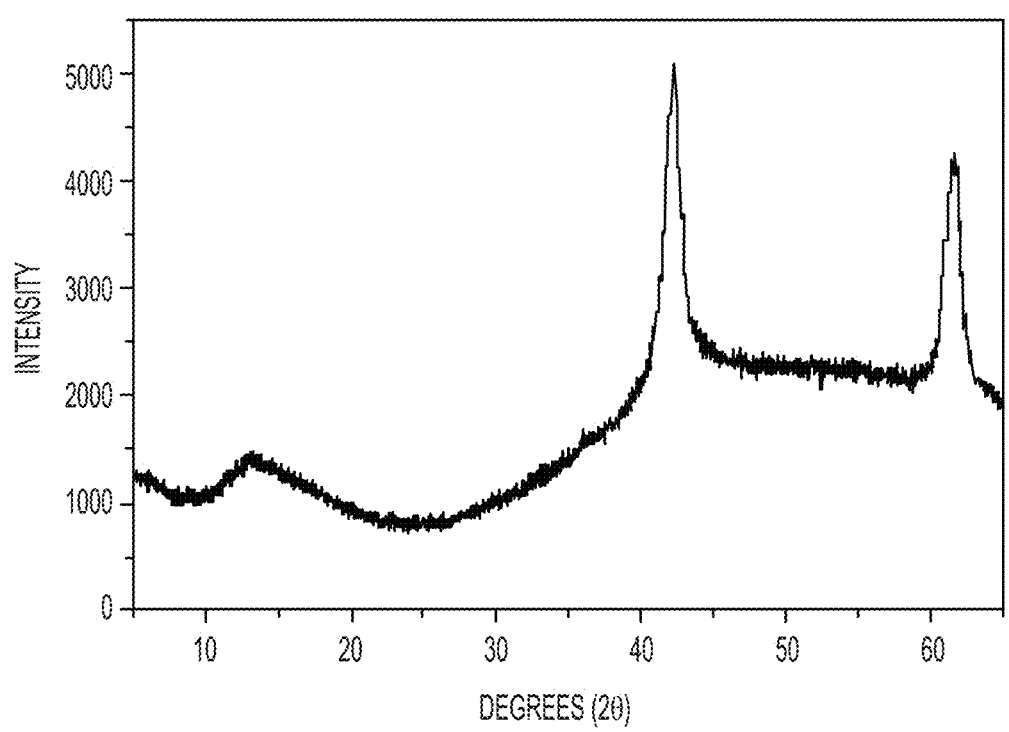
FIG. 12 is a PXRD pattern of a nanocomposite prepared by thermally decomposing Mg(1.0)-AC.
Figure 13A:
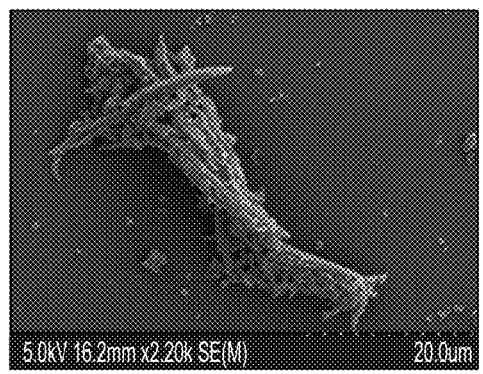
FIGS. 13A-13D are SEM micrographs at various magnifications of the nanocomposite prepared by thermally decomposing Mg(1.0)-AC.
Figure 13B:
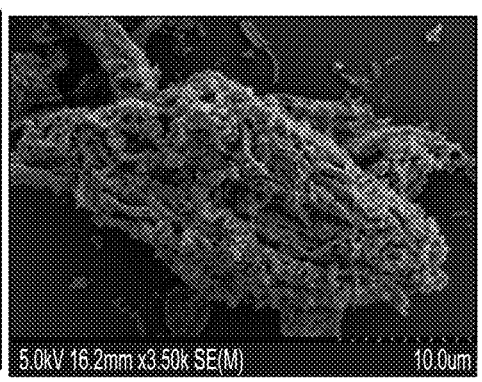
Figure 13C:
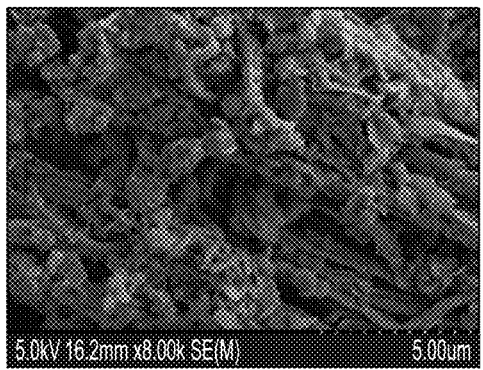
Figure 13D:
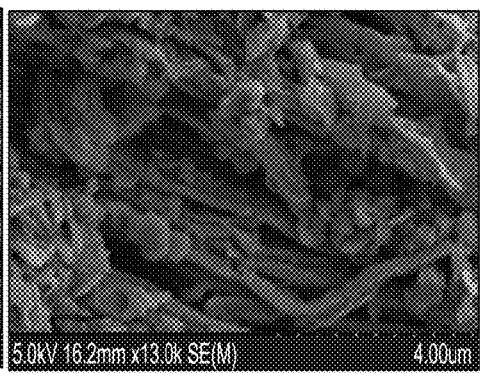

The material Mg(1.0)-AC also was subjected to thermal decomposition in a muffle furnace from room temperature to 450° C. in air atmosphere (5° C./min). The PXRD pattern of the resultant material in FIG. 12 shows MgO reflections at 2θ angles of 43.03° and 62.25°, corresponding to d-spacings of 2.1 Å and 1.49 Å, respectively. The peak at a 2θ angle of about 13° is attributable to MgO and has a larger intensity than that of the corresponding peak obtained from the thermally decomposed Mg(0.5)-AC sample. It is believed that the peak around 13° originates from the residual carbon of the adamantane moiety.

The SEM of the thermally decomposed Mg(1.0)-AC in at various magnifications in FIGS. 14A-14D show morphological differences from the thermally decomposed Mg(0.5)-AC. In the Mg(1.0)-AC, the carbon from the adamantane appears by SEM to have acted as a template for MgO to grow as bundles of long chains. This observation confirms that the polymerization of adamantane atoms occurs on thermal decomposition when confined in a narrow space of host materials. The magnesium oxide nanocomposites resulting from Mg(0.5)-AC and Mg(1.0)-AC have different morphology and crystallite sizes and, therefore, are expected to show different properties.

It should not be understood the various aspects of the composite zeolite catalyst, the method of making the same, the method of making xylene using the same, and a system for making xylene using the same are described and such aspects may be utilized in conjunction with various other aspects.

In a first aspect, the disclosure provides a method for preparing a magnesium adamantine carboxylate salt. The method comprises mixing a magnesium salt and a diamondoid compound having at least one carboxylic acid moiety to form a reactant mixture. The method further comprises hydrothermally treating the reactant mixture at a reaction temperature for a reaction time to form the magnesium adamantane carboxylate salt.

In a second aspect, the disclosure provides the method of the first aspect, in which the magnesium salt and the diamondoid compound are mixed in amounts that provide a ratio of $Mg^{2+}$ to diamondoid compound in the reaction mixture of from 0.5:1 to 1.0:1.

In a third aspect, the disclosure provides the method of the first or second aspects, in which the magnesium salt is $Mg(OH)_2$.

In a fourth aspect, the disclosure provides the method of any of the first through third aspects, in which the diamondoid compound is 1-adamantane carboxylic acid.

In a fifth aspect, the disclosure provides the method of any of the first through fourth aspects, in which the reaction temperature is from 100° C. to 180° C.

In a sixth aspect, the disclosure provides the method of any of the first through fourth aspects, in which the reaction temperature is from 140° C. to 160° C.

In a seventh aspect, the disclosure provides the method of any of the first through sixth aspects, in which the reaction time is at least 12 hours.

In an eighth aspect, the disclosure provides the method of any of the first through seventh aspects, in which the magnesium adamantane carboxylate salt comprises a layered morphology.

In a ninth aspect, the disclosure provides the method of the eighth aspect, in which the layered morphology comprises a plurality of layers lacking edge-to-face connections.

In a tenth aspect, the disclosure provides the method of the eighth or ninth aspects, in which the layered morphology comprises a plurality of layers each having aspect ratios greater than 500.

In an eleventh aspect, the disclosure provides a method for preparing a nanocomposite. The method comprises thermally decomposing a magnesium adamantane carboxylate salt prepared according to the method of any one of the first through tenth aspects to form the nanocomposite.

In a twelfth aspect, the disclosure provides the method of the eleventh aspect, in which thermally decomposing the magnesium adamantane carboxylate salt comprises heating the magnesium adamantane carboxylate salt in air at a decomposition temperature for a decomposition time.

In a thirteenth aspect, the disclosure provides the method of any of the twelfth, in which the decomposition temperature is at least 450° C.

In a fourteenth aspect, the disclosure provides the method of the twelfth or thirteenth aspects, in which the decomposition time is at least 4 hours.

In a fifteenth aspect, the disclosure provides the method of any of the eleventh through fourteenth aspects, in which the nanocomposite comprises magnesium oxide particles dispersed on a carbon support.

In a sixteenth aspect, the disclosure provides the method of any of the eleventh through fifteenth aspects, in which the nanocomposite comprises a microporous sheet morphology.

In a seventeenth aspect, the disclosure provides a catalyst system. The catalyst system comprises (a) a magnesium adamantane carboxylate salt prepared according to any of the first through tenth aspects; (b) a nanocomposite according to any of the eleventh through sixteenth aspects; or (c) a mixture of (a) and (b).

In an eighteenth aspect, the disclosure provides a method for catalyzing a chemical reaction between at least one first reactant and at least one second reactant. The method comprises reacting the at least one first reactant and at least one second reactant in the presence of a catalyst system according to the seventeenth aspect.

In a nineteenth aspect, the disclosure provides a method for catalyzing the decomposition of a reactant. The method comprises decomposing the reactant in the presence of a catalyst system according to the seventeenth aspect.

In a twentieth aspect, the disclosure provides a polymer composite. The polymer composite comprises at least one polymer or copolymer; and at least one filler material interspersed among the at least one polymer or copolymer to form a composite. The at least one filler material is chosen from (a) a magnesium adamantane carboxylate salt prepared according to any of the first through tenth aspects; (b) a nanocomposite according to any of the eleventh through sixteenth aspects; or (c) a mixture of (a) and (b).

In a twenty-first aspect, the disclosure provides a system for removing a chemical compound from a fluid stream. The system comprises an adsorbent chosen from (a) a magnesium adamantane carboxylate salt prepared according to any of the first through tenth aspects; (b) a nanocomposite according to any of the eleventh through sixteenth aspects; or (c) a mixture of (a) and (b). The system further comprises a vessel in which or on which the chemical compound in the fluid stream is contacted with the adsorbent.

It will be apparent to those skilled in the art that various modifications and variations can be made to the embodiments described in this specification without departing from the spirit and scope of the claimed subject matter. Thus it is intended that the specification cover the modifications and variations of the various embodiments described in this specification provided such modification and variations come within the scope of the appended claims and their equivalents.

Throughout this disclosure ranges are provided. It is envisioned that each discrete value encompassed by the ranges are also included. Additionally, the ranges which may be formed by each discrete value encompassed by the explicitly disclosed ranges are equally envisioned.

What is claimed is:

1. A method for preparing a magnesium adamantane carboxylate salt, the method comprising:
   mixing a magnesium salt and a diamondoid compound having at least one carboxylic acid moiety to form a reactant mixture; and
   hydrothermally treating the reactant mixture at a reaction temperature for a reaction time to form the magnesium adamantane carboxylate salt.

2. The method of claim 1, wherein the magnesium salt and the diamondoid compound are mixed in amounts that provide a ratio of $Mg^{2+}$ to diamondoid compound in the reaction mixture of from 0.5:1 to 1.0:1.

3. The method of claim 1, wherein the magnesium salt is $Mg(OH)_2$.

4. The method of claim 1, wherein the diamondoid compound is 1-adamantane carboxylic acid.

5. The method of claim 1, wherein the reaction temperature is from 100° C. to 180° C.

6. The method of claim 1, wherein the reaction temperature is from 140° C. to 160° C.

7. The method of claim 1, wherein the reaction time is at least 12 hours.

8. The method of claim 1, wherein the magnesium adamantane carboxylate salt comprises a layered morphology.

9. The method of claim 8, wherein the layered morphology comprises a plurality of layers lacking edge-to-face connections.

10. The method of claim 8, wherein the layered morphology comprises a plurality of layers each having aspect ratios greater than 500.

11. A method for preparing a nanocomposite, the method comprising:
    thermally decomposing a magnesium adamantane carboxylate salt to form the nanocomposite;
    the magnesium adamantane carboxylate salt prepared by:
        mixing a magnesium salt and a diamondoid compound having at least one carboxylic acid moiety to form a reactant mixture; and
        hydrothermally treating the reactant mixture at a reaction temperature for a reaction time to form the magnesium adamantane carboxylate salt.

12. The method of claim 11, wherein thermally decomposing the magnesium adamantane carboxylate salt comprises heating the magnesium adamantane carboxylate salt in air at a decomposition temperature for a decomposition time.

13. The method of claim 12, wherein the decomposition temperature is at least 450° C.

14. The method of claim 12, wherein the decomposition time is at least 4 hours.

15. The method of claim 11, wherein the nanocomposite comprises magnesium oxide particles dispersed on a carbon support.

16. The method of claim 11, wherein the nanocomposite comprises a microporous sheet morphology.

17. A catalyst system comprising:
    (a) a magnesium adamantane carboxylate salt prepared by:
        mixing a magnesium salt and a diamondoid compound having at least one carboxylic acid moiety to form a reactant mixture; and
        hydrothermally treating the reactant mixture at a reaction temperature for a reaction time to form the magnesium adamantane carboxylate salt;
    (b) a nanocomposite prepared by:
        thermally decomposing the magnesium adamantine carboxylate of (a) to form the nanocomposite; or
    (c) a mixture of (a) and (b).

* * * * *